United States Patent [19]

McMillin et al.

[11] 4,074,809
[45] Feb. 21, 1978

[54] APPARATUS AND METHODS FOR INSPECTION OF CAN BODIES BY USE OF LIGHT

[75] Inventors: Danny Leon McMillin, Golden; Larry Mason Dugan, Boulder, both of Colo.

[73] Assignee: Coors Container Company, Golden, Colo.

[21] Appl. No.: 706,478

[22] Filed: July 19, 1976

[51] Int. Cl.² ............................................. B07C 5/344
[52] U.S. Cl. ................................ 209/75; 209/111.7 T
[58] Field of Search ............... 209/111.7, 111.5, 111.6, 209/75; 73/45, 45.1, 45.2, 45.4; 356/240, 237

[56] References Cited

U.S. PATENT DOCUMENTS

| | | | |
|---|---|---|---|
| 2,919,801 | 1/1960 | Pechy | 209/111.7 |
| 3,159,279 | 12/1964 | Sloan et al. | 209/111.5 |
| 3,416,659 | 12/1968 | Linderman et al. | 209/111.7 R |
| 3,453,054 | 7/1969 | Phillips | 356/237 |
| 3,750,877 | 8/1973 | Dracho et al. | 209/73 |
| 3,886,353 | 5/1975 | Shioya | 356/240 |

*Primary Examiner*—Allen N. Knowles
*Attorney, Agent, or Firm*—Bruce G. Klaas

[57] ABSTRACT

Apparatus and methods for testing printed metallic can body members for defects by the use of light involving gravity infeed apparatus for locating can body members in separate pockets on a continuously rotating transfer wheel, seating apparatus for seating the can body members in the pockets, testing the exterior surface of the can body member for the presence of printed ink thereon, axially displaceable can body member support apparatus for axial displacement of the can body members relative to the pockets and the transfer wheel to locate a flange portion in sealed association with a resilient deflectable sealing member, application of vacuum to the bottom of the can body member to hold the can body member on the support apparatus until release of the vacuum, application of pressure to and pressurization of the sealing member and the inside of the can body member; location of the pressurized can body member in a zone of florescent light, location of the can body member relative to light detecting apparatus in the light zone to detect any light passing through the walls and through or around the flange portion of the container body member, retracting the can body member from sealed association with the sealing member, first discharging defective can body members into discharge chute apparatus by gravity after release of vacuum, and then unloading acceptable can body members into unloading chute apparatus by gravity after release of vacuum.

57 Claims, 14 Drawing Figures

FIG_5

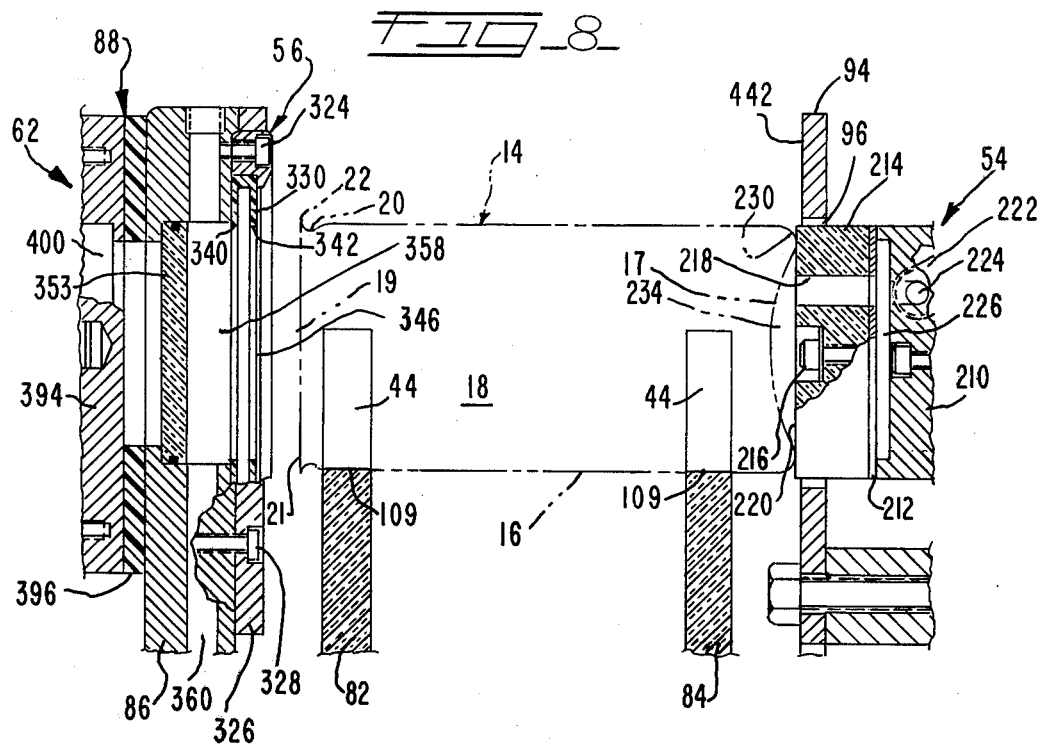
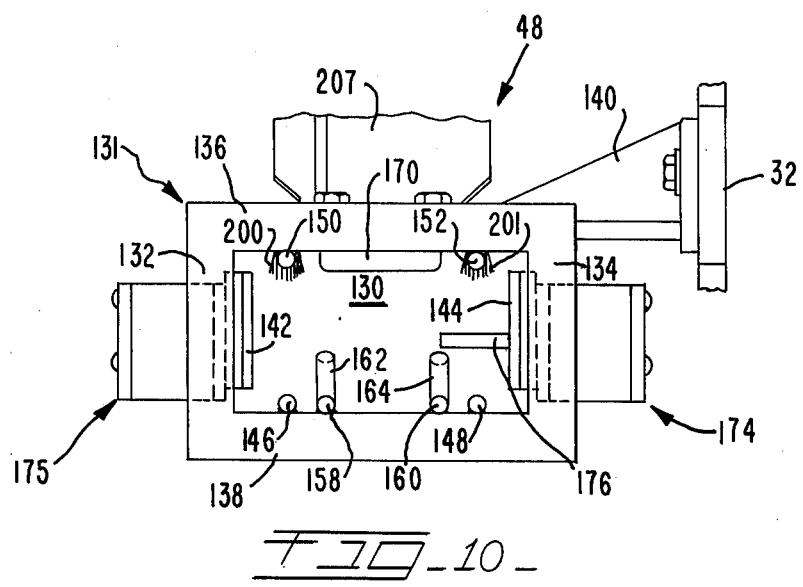

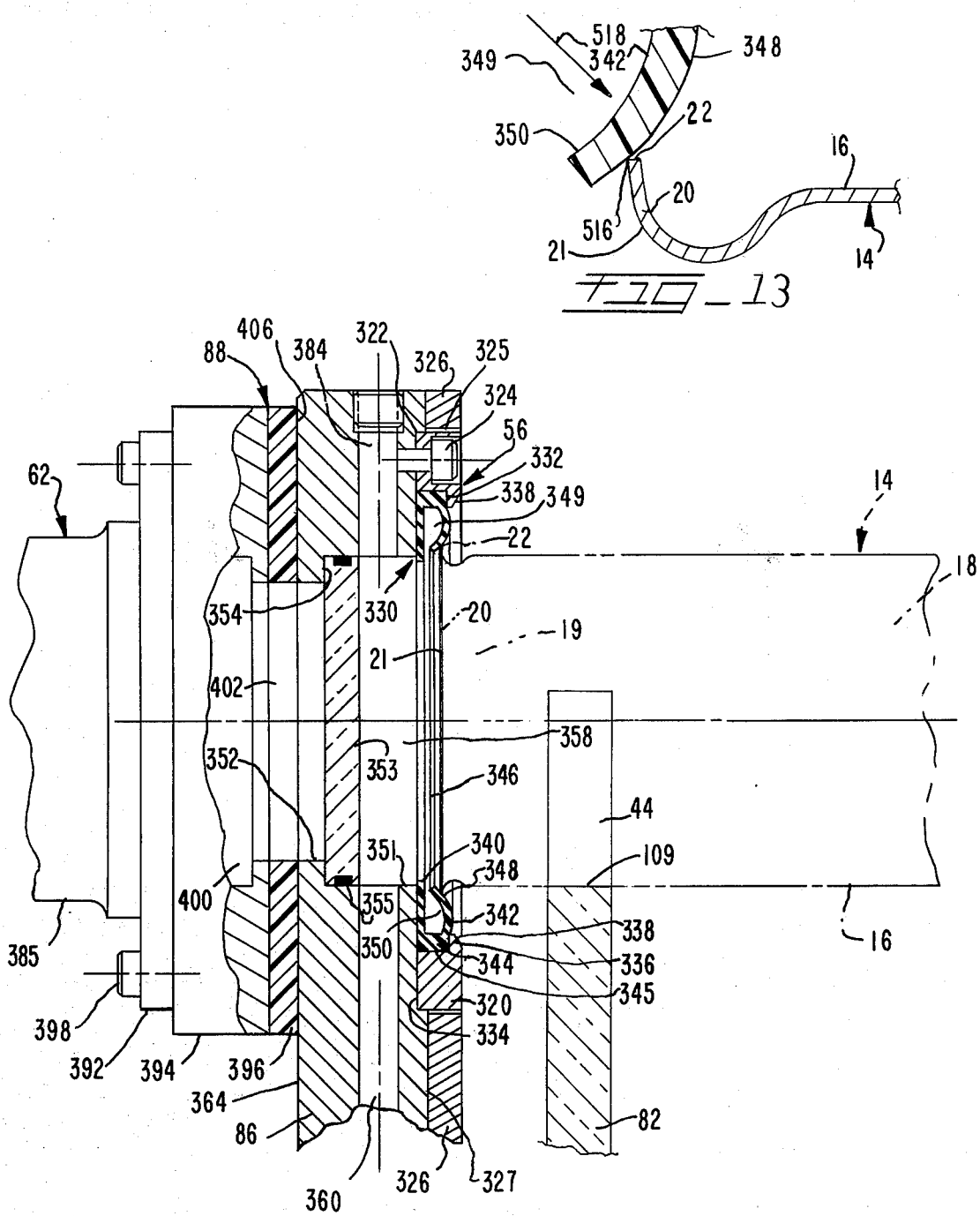

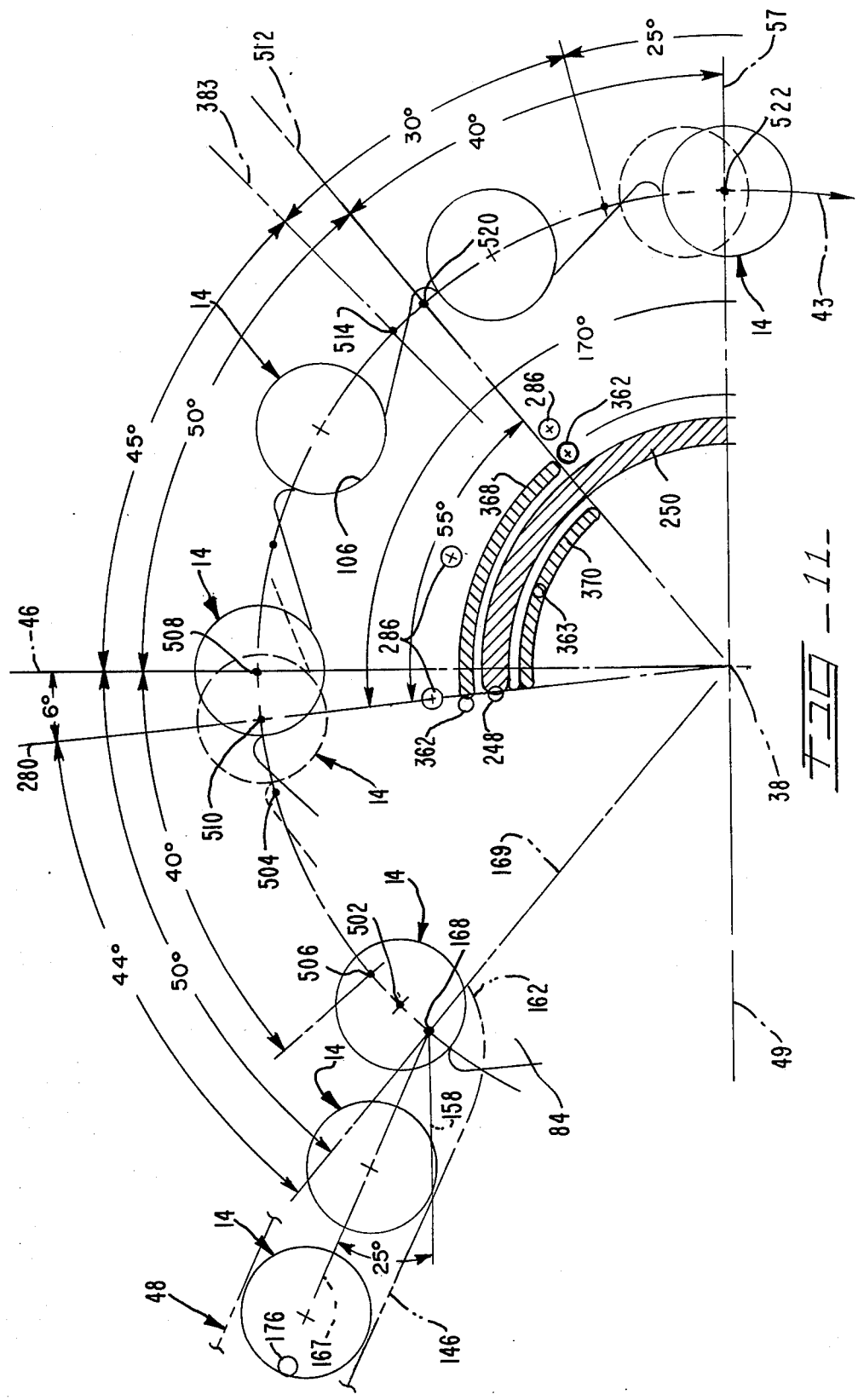

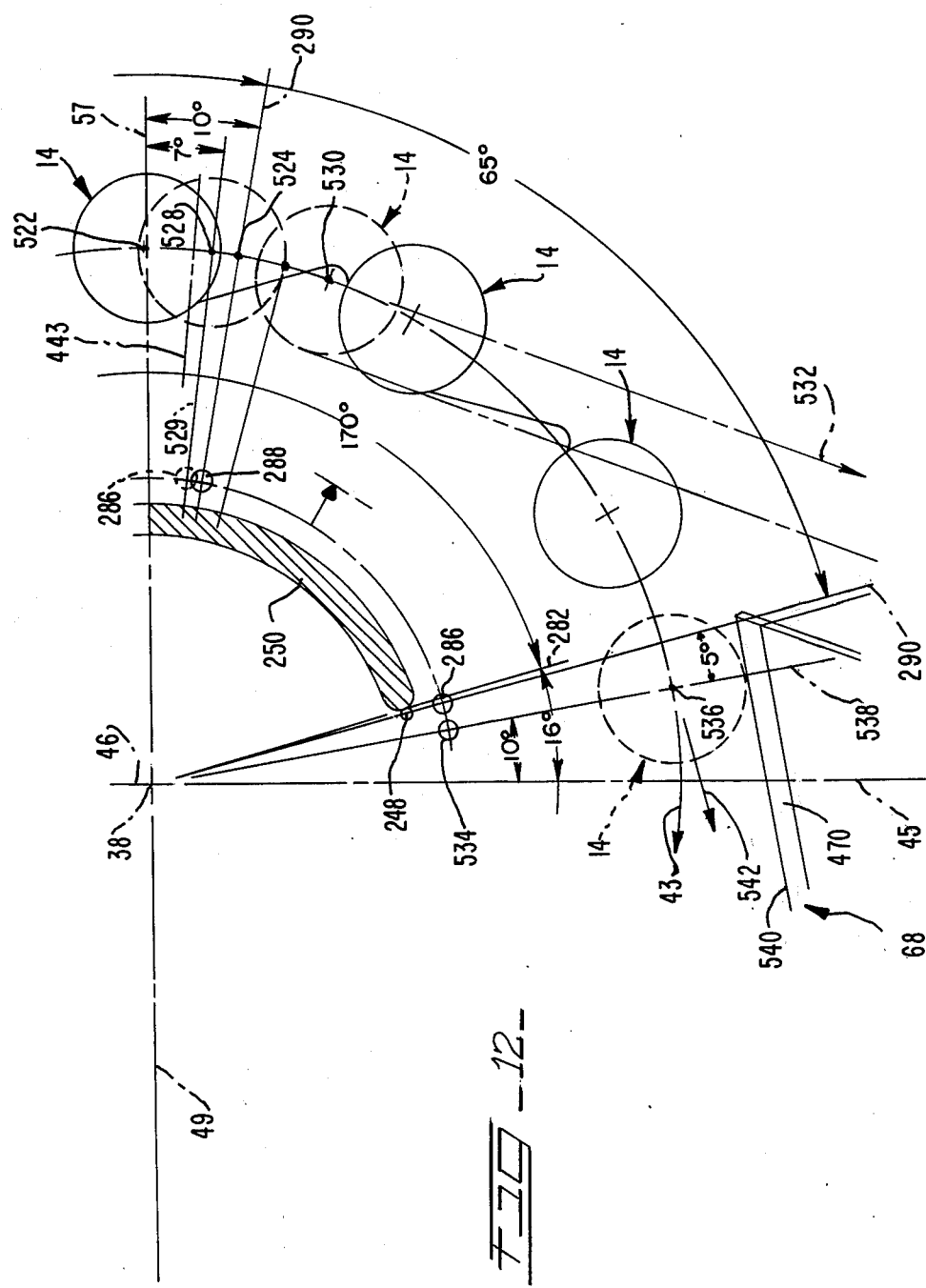

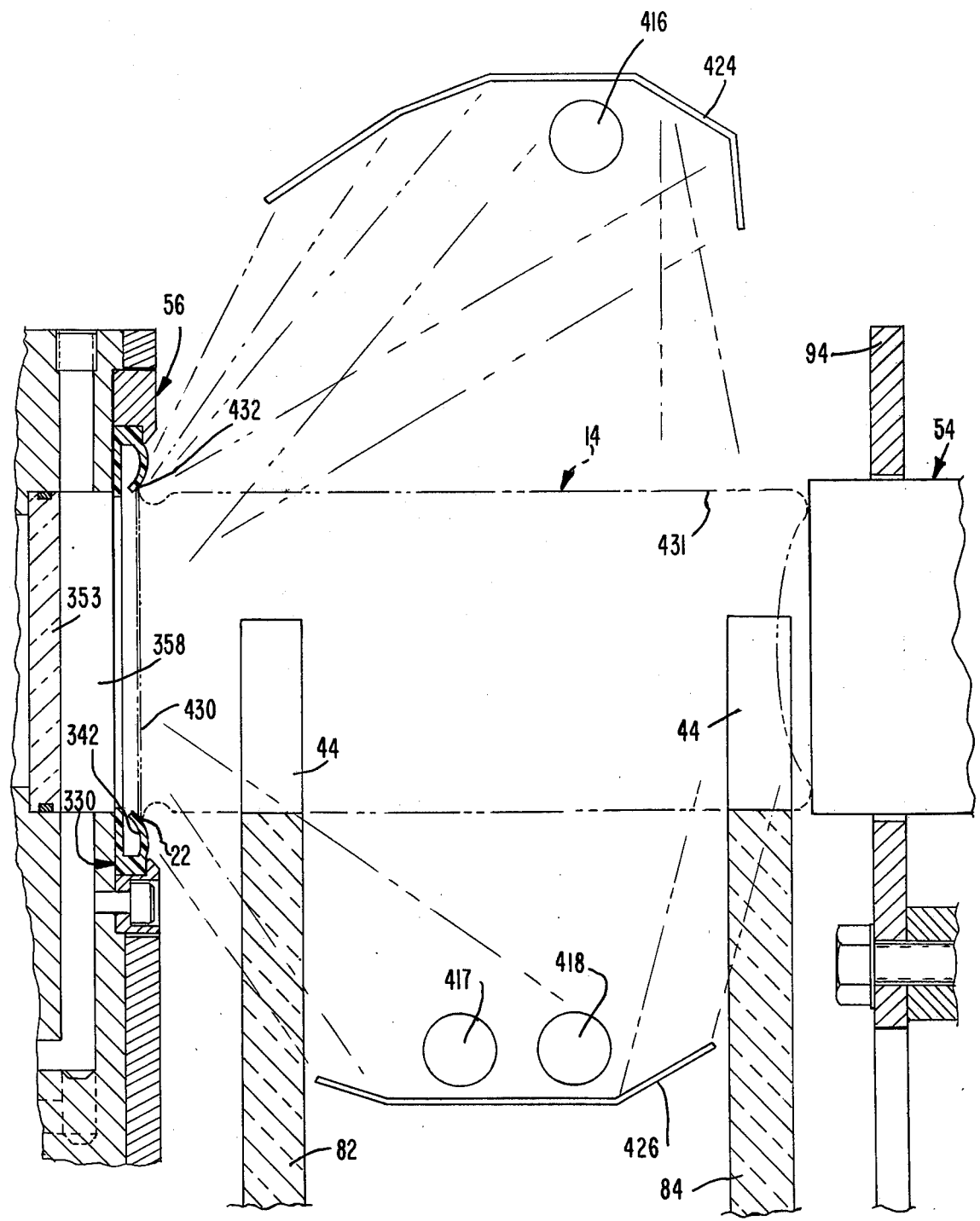
FIG_14

APPARATUS AND METHODS FOR INSPECTION OF CAN BODIES BY USE OF LIGHT

BACKGROUND AND SUMMARY OF THE INVENTION

This invention relates to apparatus and methods for testing the walls and rims of containers and, more particularly, to apparatus and methods for testing metallic can body members for defects by the use of light.

The use of light to test containers and container materials has been known since at least 1908 as evidenced by U.S. Pat. No. 901,393 and many patents have been granted in the field, including U.S. Pat. Nos. 1,965,819; 2,229,451; 2,246,906; 2,318,856; 2,453,720; 2,481,863; 2,561,406; 2,563,213; 2,682,802; 2,729,136; 2,750,519; 2,872,039; 3,107,011; 3,159,279; 3,171,033; 3,327,849; 3,328,000; 3,416,659; 3,453,054; and 3,750,877.

The present invention relates to new and improved apparatus and methods of the general type disclosed in U.S. Pat. No. 3,750,877 in which metallic can body members are carried by a continuously rotating transfer wheel to a defect detection station whereat the open end or ends of a can body are brought into sealing engagement with sealing means, the exterior surfaces of the can body are flooded with light from a light source; and a light sensing device detects any light passing through the exterior surfaces of the can body to activate reject means to segregate defective can body members from satisfactory can body members.

Until the present invention, no light testing apparatus has been available which provided completely satisfactory results in terms of high speed accurate testing of both the walls and flange portions of can body members, relatively low cost construction, easy maintenance, and reliability in use with minimum down time for maintenance and repairs. A primary problem in the manufacture of can body members, such as, for example, one piece thin wall aluminum sheet metal can body members, is maintaining defect free flange portions. Small, e.g., 0.005 or larger, edge cracks in the flange portion may cause leaks in cans during completion of a can by association of end closing members with the can body members by application of relatively high forces to effect closure of the can body members. In addition, it is desirable to detect pin holes at least as small as 0.001 inch in the walls of the can body members which could cause leaks in use. In the beer industry, some beer manufacturers pasteurize the beer after a can has been filled and sealed, while other manufacturers do not pasteurize the beer. Often times the heat and pressure of the pasteurization process will reveal leaks in the finished cans by causing some of the contents to be driven through the cracks so that leaking cans may be visually observed and removed from the production line. However, if there is no pasteurization process, the leaks may not be detected at the time of manufacture and the leakage may contaminate or spoil adjacent containers or packages while in addition the product may deteriorate or spoil prior to consumption. Thus, in order to maintain high quality standards, it is imperative that all possible defects which may produce leaks be detected prior to completion of the can and filling of the can with the contents.

In addition, the testing apparatus is arranged and constructed so that damaged portions of the can body member other than the flange which cause the bottom peripheral rim surface to be other than in a flat condition will also be detected and rejected due to loss of vacuum by which the can body members are held during the transfer process.

The present invention provides for inspection of can body members with nearly 100% detection of such defects. It is contemplated that the percentage of successful detection of such defects is such that, on the average, approximately only one defective can body member in one million will not be detected and ejected by the testing apparatus. In addition, the present invention provides testing apparatus which is continuously operable at relatively high speeds up to or in excess of 1000 can body members per minute. Furthermore, the cost of manufacture of the testing apparatus has been substantially reduced as compared with apparatus of the type disclosed in U.S. Pat. No. 3,750,877 with maintenance, repair, and down time substantially improved to increase overall reliability. In addition, the present invention provides printing detection means for determining the presence or absence of a printed label on the exterior surface of the can body member.

Another feature of the present invention resides in the provision of new and improved light source means for flooding the exterior surfaces of the can body members with light in the test position without requiring the use of light reflective surfaces on the apparatus as have been used in prior art apparatus. In the present invention a relatively few florescent lamps are utilized, such as six to seven, whereas prior art apparatus has employed as many as 19 ultraviolet lamps including the extensive use of reflective apparatus surfaces in order to achieve satisfactory results. Instead of using reflective apparatus surfaces, it has been determined that by proper positioning of a relatively small number of lamps, and in particular florescent lamps with associated lamp reflectors and black anodization of surrounding metallic surfaces, exceptionally good results can be obtained.

In addition, the present invention provides uniform light intensity around the entire can body member by particular arrangement and spacing of the lamps. Other features of the present invention include supporting the can body members by vacuum applied to the outside bottom wall, internal pressurization of the can body member during testing, discharge of defective can body members only by inertial forces and gravity after release of vacuum, and removal of acceptable can body members directly from the transfer wheel to gravity discharge chute apparatus.

In general, the inventive concepts involve the use of a new and improved gravity feed system; a new and improved can body flange sealing system with pressurization of the seal and the can body during inspection; a new and improved lighting system; a new and improved mounting of a light detector device relative to a continuously rotating transfer wheel; new and improved ejection apparatus for removal of defective can body members from the transfer wheel; and new and improved transfer apparatus for removing non-defective acceptable can body members from the transfer wheel.

BRIEF DESCRIPTION OF THE DRAWING

The inventive concepts are illustrated in apparatus comprising a presently preferred embodiment thereof on the accompanying drawing in which:

FIG. 8 is an enlarged cross-sectional view of a portion of the apparatus of FIG. 4 enclosed by the dashed line 8—8 prior to sealing association of the can body member with a sealing means;

FIG. 9 is an enlarged cross-sectional view of the portion of the apparatus of FIG. 4 enclosed by the dashed line 8—8 after sealing association of the can body member with the sealing means;

FIG. 10 is an enlarged end view of a portion of the apparatus taken along the line 10—10 in FIG. 6;

FIGS. 11 and 12 are enlarged schematic representations of portions of the apparatus illustrating the sequence of operation thereof;

FIG. 13 is an enlarged cross-sectional view of a portion of the sealing means and a portion of the can body member of FIG. 9; and FIG. 14 is an enlarged cross-sectional view of a portion of the apparatus of FIG. 6.

DETAILED DESCRIPTION

In General

Figure 1:
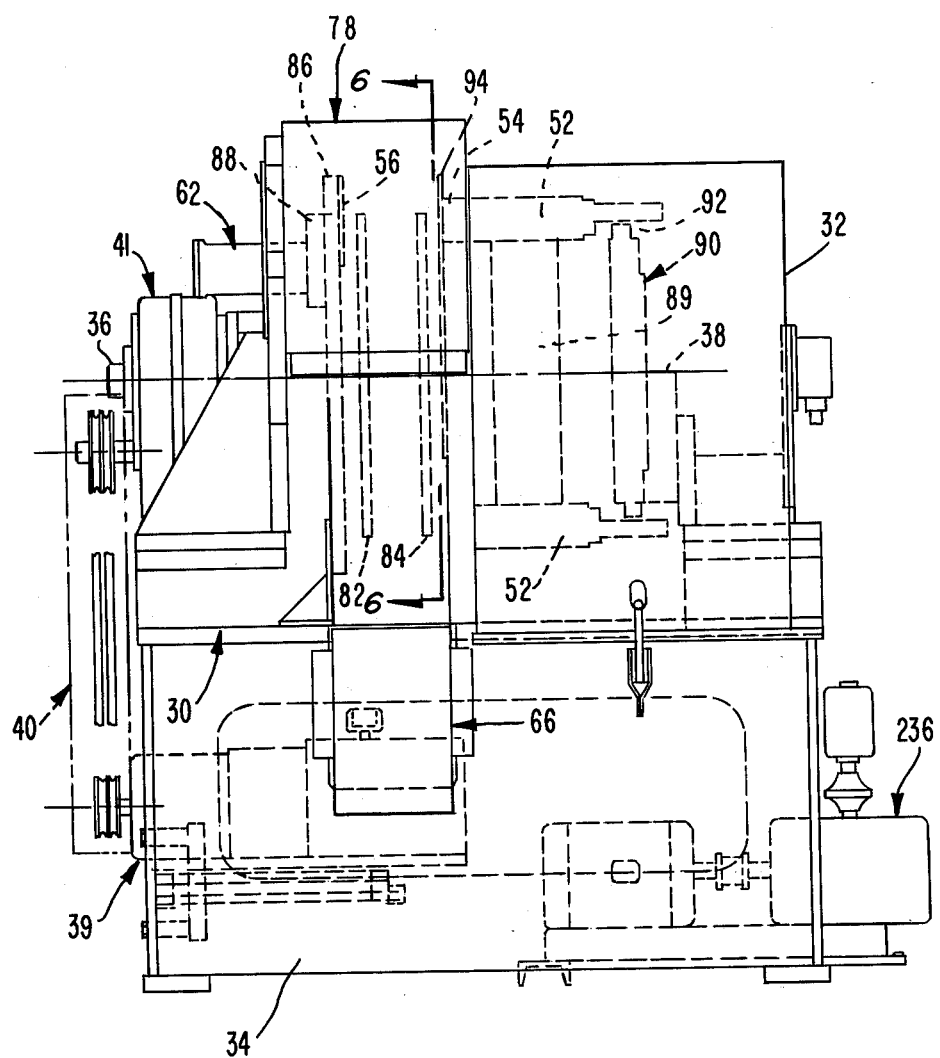
FIG. 1 is a side elevational view of the apparatus.

While certain of the inventive concepts are applicable to apparatus for testing any tubular member for sidewall defects, such as pin holes, or for flange defects, such as cracks, the present invention is particularly adapted for testing of one piece aluminum can body members 14 utilized for manufacture of two piece aluminum cans. As shown in FIGS. 8 and 9, such one piece aluminum can body members comprise an annular sidewall portion 16, closed at one end by an inwardly domed concave bottom wall portion 17, to define a container cavity 18, while having an annular opening 19 at the opposite end surrounded and defined by a formed generally radially outwardly extending annular flange portion 20 having a generally radially extending outer side surface 21 terminating in an annular edge portion 22. Such can body members are conventionally utilized to package beer, soft drinks, and other products by filling the container cavity 18 with the product and then sealingly attaching an end closure member over the opening 19 in sealed association with the flange portion 20 which is further deformed during the attachment process to effect a sealed relationship with the end member. In addition, the outer peripheral surface of sidewall portion 16 conventionally has a label of printed ink applied thereto.

It is desirable to inspect such can body members for "defects" prior to filling the can body member with the product to be packaged therein and prior to associating the end closure member therewith. Among the various "defects" in the can body member which should be preferably detected before filling and closing are: (1) Any pin holes which will prevent complete sealing of the contents; (2) any cracks or deformation in the flange portion 20 which will prevent proper sealed association with the end closure member; (3) any dents or deformation in the sidewall portion 16 which may affect the round annular conditions of the flange portion 20 and, hence, prevent proper sealed association with the end closure member or the appearance of the finished filled container; and (4) the absence of a printed ink label on the outer peripheral surface of the sidewall portion 16.

Figure 3:
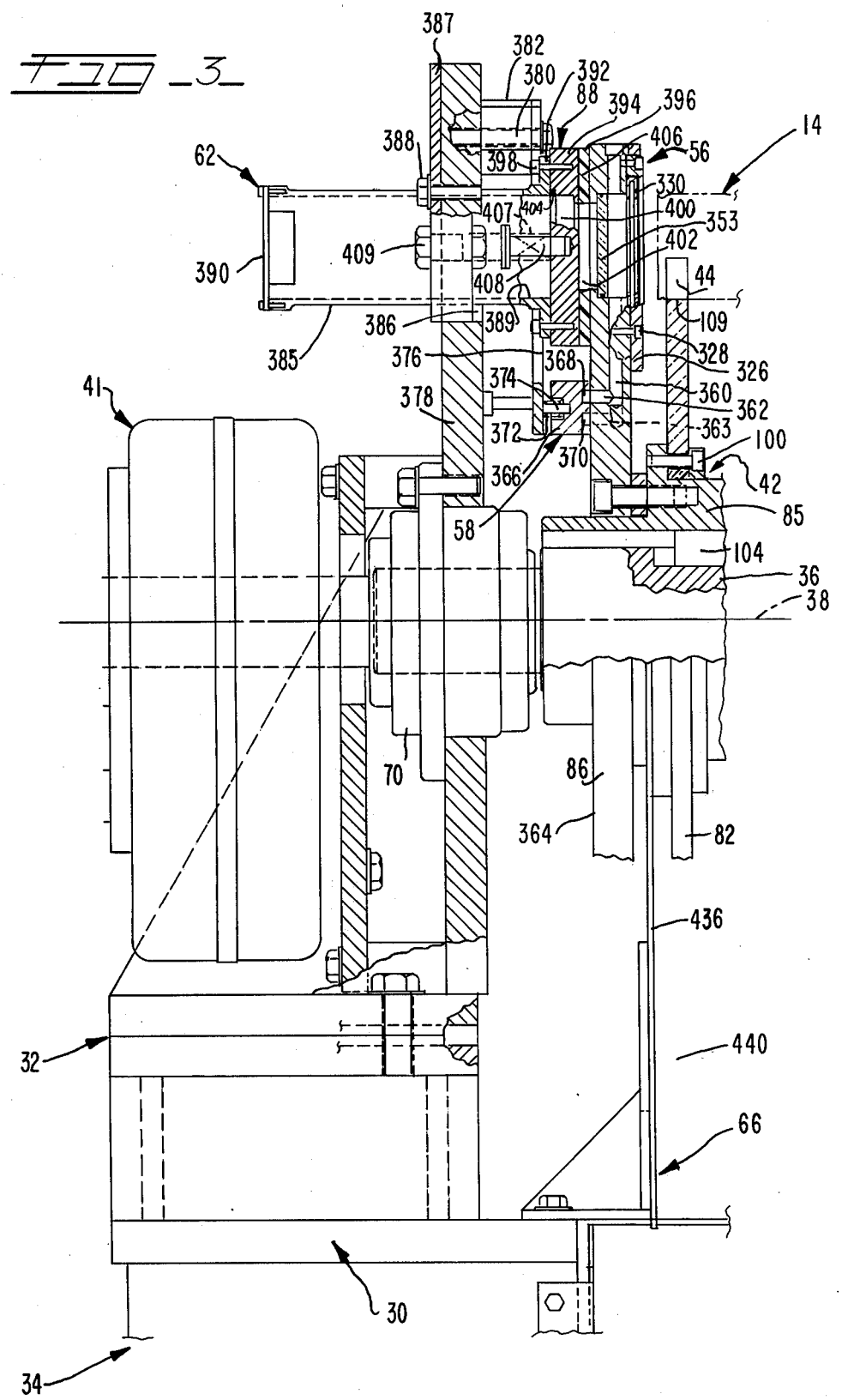
FIG. 3 is an enlarged partial cross-sectional side elevational view of the left hand portion of the apparatus of FIG. 1 taken along line 3—3 in FIG. 2.
Figure 6:
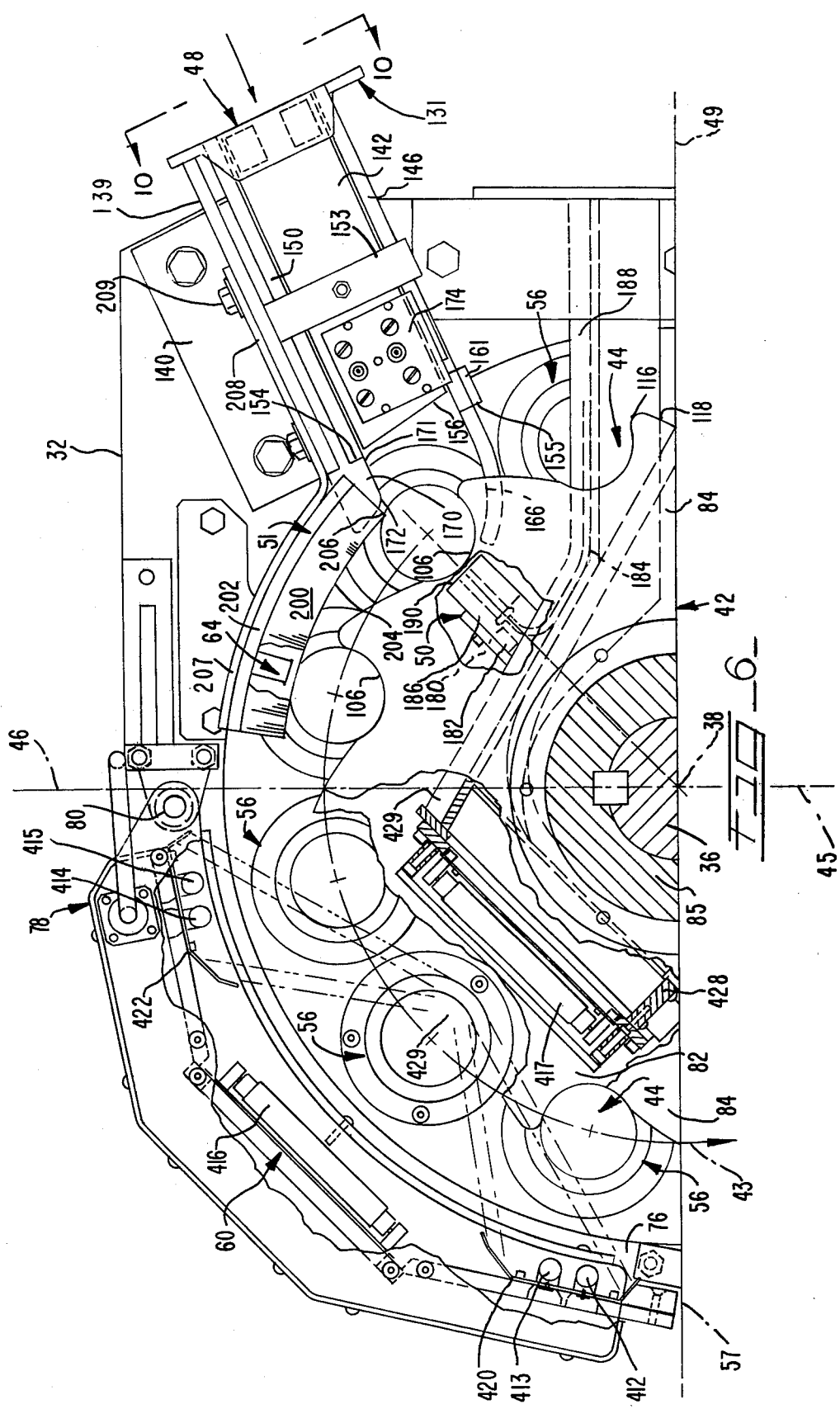
FIGS. 6 and 7 are enlarged partial cross-sectional views, with parts removed, taken along the line 6—6 in FIG. 1.
Figure 7:
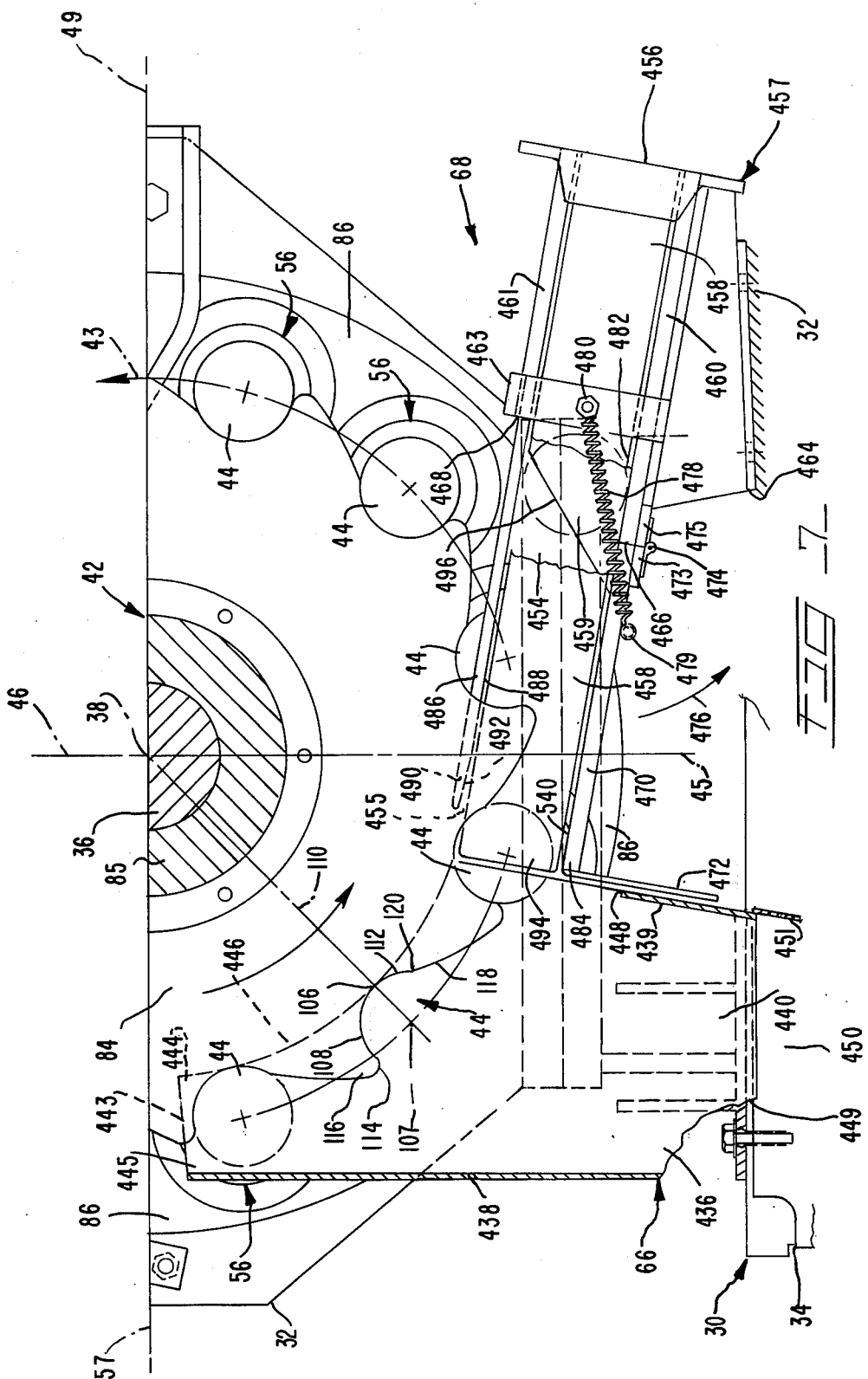

In general, the presently preferred embodiment of the invention shown in the accompanying drawing comprises: frame and housing means 30 having upper and lower portions 32, 34 for the machine components; horizontally extending rotatable drive shaft means 36 for continuous rotation of various machine components about a central axis of rotation 38; electric motor means 39, belt-pulley drive means 40, and speed reducer means 41 for causing continuous rotation of the rotatable shaft means; can body member transfer wheel means 42 mounted on the rotatable shaft means for continuous rotation therewith and for carrying can body members in a circular path 43, FIGS. 6 and 7, in the direction of the arrows thereabout; a plurality of pocket means 44 circumferentially spaced about the outer periphery of said transfer wheel means for receiving a can body member 14 and supporting the can body member sidewall portion 16 in each pocket means, there being twelve axially spaced pairs of such pocket means in the illustrative embodiment, and for transferring each can body member along the circular path of movement only during a portion of each revolution of the transfer wheel means with each pocket means being carried generally upwardly between lower vertical center line 45 and upper vertical center line 46 during 180° of each revolution and generally downwardly during the other 180° of each revolution of the transfer wheel means; infeed means 48 non-rotatably mounted on the frame and housing means for loading one can body member in each of the pocket means during the last 90° of the generally upward movement of the pocket means between horizontal center line 49 and upper vertical center line 46 during each revolution; empty pocket detection means 50, FIG. 6, for providing a control signal whenever no can is placed in the pocket means 44 at the infeed means 48; non-rotatable seating means 51, mounted in juxtaposition to the infeed means for seating each can body member on a surface of each of the pocket means during the last 90° of the generally upward movement of the pocket means between center lines 49, 46 during each revolution; extendable and retractable means 52, FIG. 1, mounted on the drive shaft means for rotation therewith, there being one such means for each of the pocket means, and for axially moving each can body member in each of the pocket means between a first axially retracted position and a second axially extended position during each revolution; releasable holding means 54 associated with each of the axially extendable and retractable means for abutting and releasable holding engagement with the bottom wall portion of each can body member in each of the pocket means during predetermined portions of each revolution; flange portion sealing means 56 associated with each of the axially extendable and retractable means and each of the pocket means and being mounted on the drive shaft means for rotation therewith and for sealable engagement with the flange portion 20 of each can body member carried in each of the pocket means during the first 90° of the generally downward movement of the pocket means between upper vertical center line 46 and horizontal center line 57, FIG. 6, during each revolution; pressurization means 58, FIG. 3, associated with each of the sealing means for applying pressurized air to the sealing means for obtaining a minimum area of sealable engagement between the sealing means and the flange portion 20 of each can body member and for applying pressurized air through the can body member opening 19 to the container cavity 18 to apply outwardly directed force on the interior surfaces of the can body member to outwardly flex the sidewall portion 16 and the bottom wall portion 17 to enhance the detection of pin holes by passage of light therethrough; non-rotatable light applying means 60, FIG. 6, for applying light to the exterior surfaces of each pressurized can body member in each of the pocket means in sealable association with the sealing means and being located to provide a continuous light zone during the first 90° of the generally downward movement of the pocket means during each revolution; light detection means 62, FIG. 1, non-rotatably mounted relative to the transfer wheel means and the sealing means and being located for successive axial alignment with each of the pocket means, after sealable association of the flange portion with the sealing means and pressurization of the sealing means and the can body member carried in the pocket means, in the light zone for receiving light only from the light applying means through the can body member and/or between the flange portion and the sealing means, and for generating a first defective can control signal upon receipt of light to provide an indication of a defective can body member; non-printed can body member detection means 64, FIG. 6, non-rotatably mounted relative to the transfer wheel means and located in juxtaposition to the seating means and adjacent the outer peripheral surface of the sidewall portion 16 of each can body member while being carried by the pocket means along the circular path for providing a second defective can control signal in response to light reflected from the outer peripheral surface of non-printed can body members; defective can body member discharge chute means 66, FIG. 7, for receiving defective can body members from the pocket means on the transfer wheel means during only the last 90° of the generally downward movement of the pocket means between horizontal center line 57 and lower vertical center line 45 during each revolution; and non-defective can body member unloading chute means 68, FIG. 7, for receiving non-defective can body members from the pocket means on the transfer wheel means during only the last part of the last 90° of the generally downward movement of the pocket means during each revolution.

Figure 2:
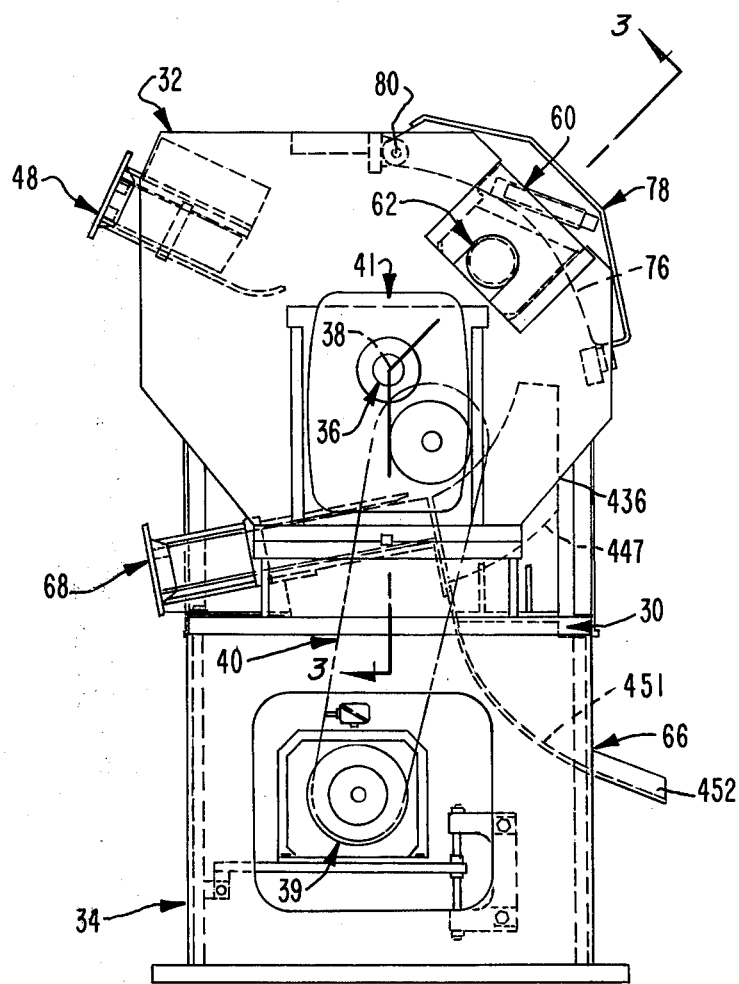
FIG. 2 is an end view of the apparatus of FIG. 1.

Referring now to FIGS. 1 and 2, in general, the test apparatus is mounted in relatively compact frame and housing means 30 comprising a lower motor and control housing portion 34 and an upper test apparatus portion 32. In the illustrative embodiment the housing means has a height of 51 inches, a length of 46 inches, and a width of 29 inches. The conventional electric motor-transmission means 39 is drivably connected by the conventional belt-pulley means 40, and the conventional speed reducer box 41 to the central axially extending shaft means 36 rotatably supported by suitable bearing means 70, 72, FIGS. 3–5.

The rotatable can body member transfer wheel means 42 is fixedly mounted on a central portion of shaft means 36 for continuous rotation therewith in a closed or partially closed generally annular test chamber 74 having an access opening 76, FIG. 3, closable by a light sealing door means 78 pivotally mounted at 80, FIG. 2

The transfer wheel means 42 comprises a pair of axially spaced annular transparent plate members 82, 84 on which the plurality of peripheral circumferentially spaced and coaxially aligned can body receiving pocket means 44, FIGS. 6 and 7, are provided. A hub member 85 fixedly mounts the plate members 82, 84 on shaft means 36 for continuous rotation therewith.

The sealing means 56 are rotatably carried by an annular sealing wheel means 86, and peripherally mounted thereon in circumferentially spaced coaxially aligned relationship with pockets 44. Wheel means 86 is fixedly mounted on shaft means 36 by hub member 85 for continuous rotation therewith and located in axially spaced relationship to transfer wheel member 82.

The light detector means 62 is fixedly mounted on the side wall of chamber 74 and extends axially into chamber 74 with a sealing head means portion 88 coaxially alignable with sealing means 56 and mounted in sealed engagement with the adjacent side surface of sealing wheel means 86.

Figure 5:
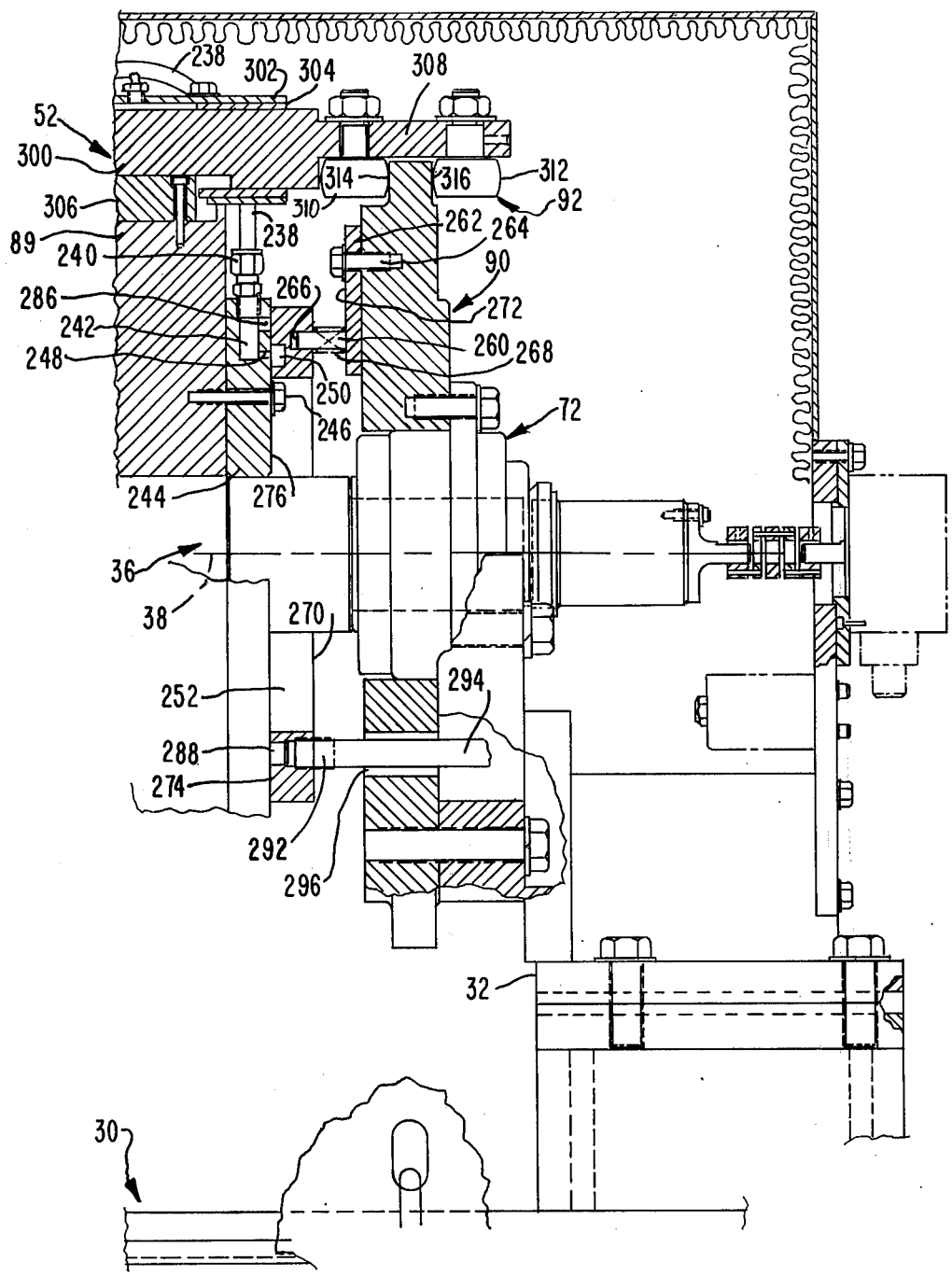
FIG. 5 is an enlarged partial cross-sectional view of the right hand portion of the apparatus of FIG. 1 axially next adjacent the apparatus shown in FIG. 4.

The releasable holding means 54 are coaxially mounted on the ends of the extendable and retractable means 52 in circumferentially spaced and coaxial alignment with pockets 44. The releasable holding means 54 and extendable and retractable means 52 are fixedly mounted on shaft means 36 by a hub member 89 for continuous rotation therewith in axially spaced relationship to transfer wheel member 84. A cam plate means 90, FIG. 5, is fixedly mounted relative to shaft means 36 for camming engagement with cam follower means 92 to extend and retract means 52. A can body member guide plate means 94 is fixedly mounted on hub member 89 for continuous rotation with shaft means 36 and has a plurality of circumferentially spaced openings 96, FIG. 8, coaxially aligned with holding means 54 to enable axial movement of the holding means therethrough.

TRANSFER WHEEL MEANS AND POCKET MEANS

Figure 4:
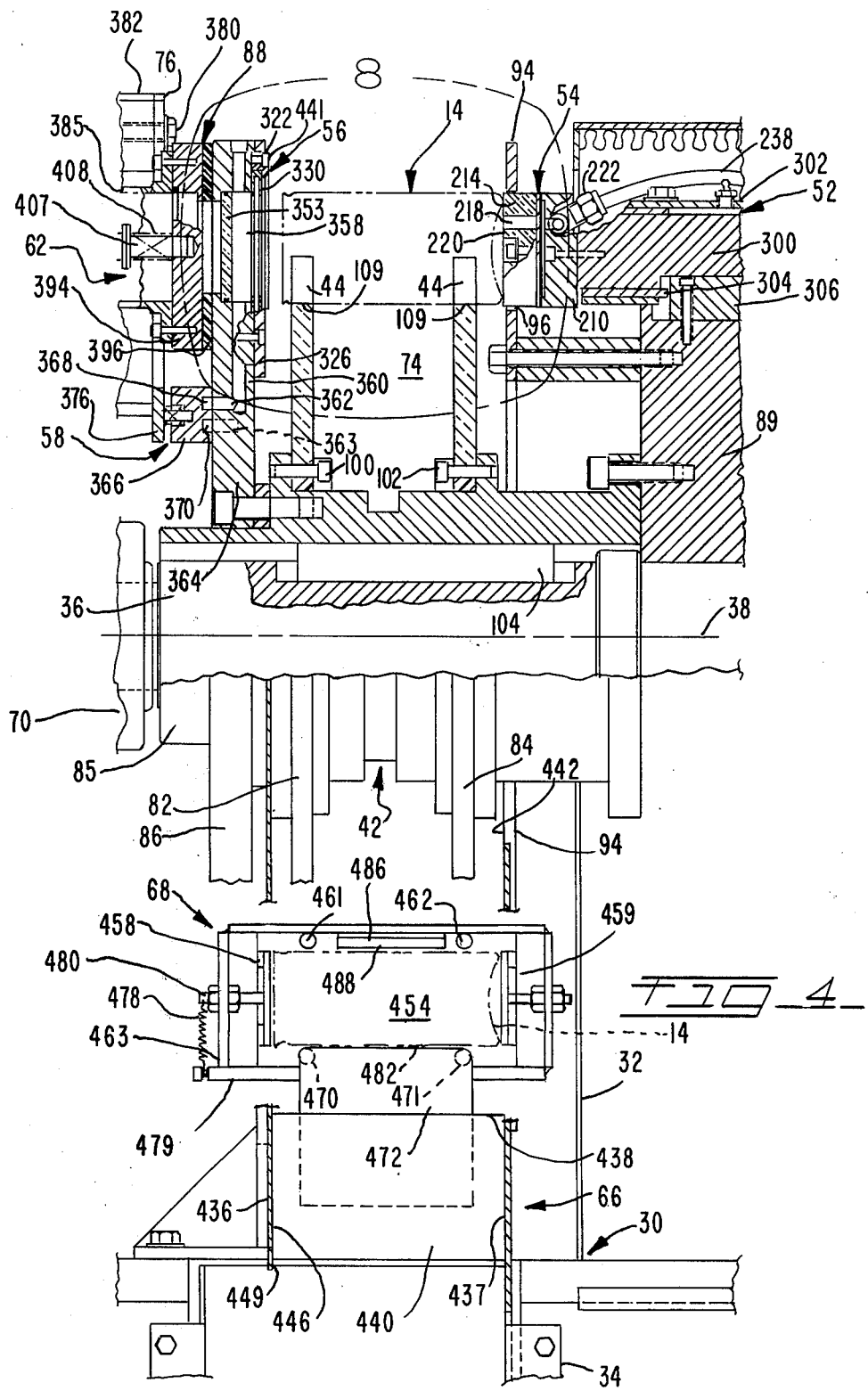
FIG. 4 is an enlarged partial cross-sectional side elevational view of an intermediate portion of the apparatus of FIG. 1 axially next adjacent the apparatus shown in FIG. 3.

Referring now to FIGS. 3 and 4, the plate members 82, 84 of the transfer wheel means 42 are of identical construction and each may be made of one piece or mating semi-cylindrical segments, of suitable transparent material, such as Plexiglas or Lucite, to enable uniform transmission of light to the entire outer surface of the can body members during testing. The plate members 82, 84 are fixedly attached to hub member 85 by a plurality of suitable fastening members 100, 102 and hub member 85 is fixedly attached to shaft means 36 by a key member 104.

In the presently preferred and illustrative embodiment, each of the plate members 82, 84 has twelve pockets 44 which are equally circumferentially spaced and coaxial with the pockets of the other plate member. As shown in FIG. 7, each pocket comprises a radially formed arcuate segment surface 106 having a center of curvature located at 107 in general coaxial alignment with the holding means 54 and the sealing means 56 so that can body members supported on surface 106 will also be located in general coaxial alignment with the holding means 54 and the sealing means 56. Surfaces 106 extend circumferentially approximately 140° with a trailing surface portion 108 of approximately 95° on the trailing side of a radial line 110, extending from the central axis of shaft 36, and a leading portion 112 of approximately 45° on the leading side of radial line 110. The trailing surface portion 108 merges tangentially with a radial surface 114 of a radially outermost cam lobe portion 116 of the plate members. The leading surface portion 112 intersects an elongated curved surface portion 118 to provide a slight transition shoulder at 120. The cam lobe portion 116 extends radially outwardly beyond center 107 so that surface 114 is effective at the can body member loading position adjacent the infeed means 48, FIG. 6, to remove the can body member being loaded into the pocket 44 while also providing a cam surface means effective to hold the next can body member in the infeed means 48 clear until the following ramp surface 118 of the following pocket begins to engage the next can body member. Ramp surface 118 provides a cam surface means effective to gradually advance the next can body member to the following pocket. Shoulder 120 is effective as the can body member leaves the loading position and approaches the seating means 51 to properly seat the can body member on surface 106 between surfaces 114 and 118.

INFEED MEANS

Referring now to FIGS. 6 and 10, the infeed means 48 is of the upwardly inclined gravity feed guide chute type having a rectangular passage 130 generally corresponding to the shape of the can body members 14, and connected to a continuous supply of can body members by conveyor means (not shown), by an attachment bracket 131 comprising side plate members 132, 134, and upper and lower plate members 136, 138. Bracket 131 is fixedly mounted on an attachment plate portion 139 of a bracket member 140 attached to the housing and frame means 32. The can body members are rollably, slidably, guidably supported by a pair of spaced elongated adjustable guide plate members 142, 144, lower round spaced elongated guide rail members 146, 148, and upper round spaced elongated guide rail members 150, 152, which are supported at the upper end by bracket 131 and by a downward spaced bracket 153 fixedly supported on plate 139. The lower ends of upper and lower rail members 146, 148, 150, 152, terminate at 154, 155, respectively, in radially outwardly spaced relationship to the plate members 82, 84. The lower end portions of guide plates 142, 144 terminate at 156 and are inclined as shown in FIG. 6. The can body members are guided from the lower end of the passage 130 into the pockets 44 by a second guide rail means, in the form of more closely spaced lower round guide rail members 158, 160 fixedly mounted on a cross plate 161 attached to and extending between rail members 146, 148. The lower terminal portions 162, 164 of rail members 158, 160 extend inwardly between and are axially spaced from the transparent plate members 82, 94 and are upwardly curved to provide upwardly curved terminal surfaces 166 extending generally in the direction of rotation of plates 82, 84 and generally tangentially to the surfaces 106 of the pockets 44. As shown in FIG. 11, the central longitudinal axis 167 of the chute passage 130 is inclined at an angle of about 25° relative to a horizontal plane and has a common point of intersection 168 with line 43 and a radial line 169 extending from axis 38 at an angle of about 40°. The arrangement is such that can body members are rollably slidably supported in stacked abutting relationship in passage 130 and continuously fed into the rotational path of plate members 82, 84 to continuously load can body members into the pockets 44 as each set of empty pockets rotate past the guide rods 162, 164. An upper guide plate 170, FIGS. 6 and 10, is mounted on plate 139 opposite rail members 158, 160, and extends inwardly between plate members 82, 84 to provide a downwardly facing guide surface 171 terminating in a curved lower surface 172 extending generally tangentially to the cylindrical upper surface of the can body members, to further guide the can body members into proper position in the pockets 44 as the can body members are removed from the chute.

In order to provide a positive stop to selectively prevent can body members from moving downwardly through infeed means 48, a pair of oppositely aligned selectively operable holding and release means 174, 175 may be provided in the form of an extendable and retractable pin members 176, FIG. 10, actuable by solenoids between a retracted release position and an extended holding position in the chute passage 130 in abutting retaining engagement with a lowermost can body member as shown in FIG. 11.

EMPTY POCKET DETECTION MEANS

In order to provide a control signal indicating the absence of a can body member in pockets 44 after passing the infeed means, an empty pocket detection means 50, FIG. 6, in the form of a conventional magnetic field type sensor device 180 mounted in a support member 182 is connected to control means (not shown) by an electrical line 184. Member 182 is adjustably fixedly mounted on a bracket member 186 fixed to a fixed plate 188 extending inwardly between rotating plate members 82, 84. The end surface 190 of member 182 is located in a plane closely adjacent to the radially innermost surfaces 106 of pockets 44 so as to be located adjacent and effective relative to the adjacent outer cylindrical surface of the can body members.

SEATING MEANS

In order to assure positive positioning and location of the can body member in pockets 44 as it is carried from the loading position toward the testing position, a seating means 51 is provided arcuately opposite the pockets 44 along an arcuate segment of the upward path of movement of the can body member beginning at or just beyond the discharge opening defined by surfaces 166, 172 and terminating prior to the vertically uppermost position along center line 46. The seating means 51 is in the form of a pair of spaced arcuate brush segments 200, 201, FIG. 10, each of which has a multitude of resilient flexible bristle members mounted on an arcuate backing plate member 202 and extending generally radially inwardly therefrom. The bristle members terminate radially inwardly along an arcuately curved resilient flexible can body member engaging surface 204 located radially outwardly from pocket surfaces 106 a distance such as to firmly engage a substantial arcuate segment of the radially outermost outer peripheral surface of the sidewall portion 16 of each can body member carried thereby. The lower end portions 206 of the bristle members are located in cooperative relationship with the pocket surface 106 and the curved guide surface 172 so as to become effective by engagement with the can body member at about the same time as the can body member is removed from the curved surfaces 166. The resilient flexible guide means thus provided are fixedly mounted relative to the rotating plate members 82, 84 by an arcuately curved portion 207 of bracket member 208 which may be adjustably mounted on the top of plate 139 by suitable fastening means 209 to assure proper alignment and positioning relative to the pockets 44.

RELEASABLE HOLDING MEANS

Referring now to FIGS. 4 and 8, the releasable holding means 54 comprise twelve separate equally circumferentially spaced axially extendable and retractable units which are rotatable with wheel members 82, 84 in general axial alignment with pockets 44. Each unit comprises an annular mounting block member 210, a spacer member 212, and an annular transparent support plate member 214 attached to member 210 by suitable recessed fastening means 216. A vacuum and air passage 218 extends axially through flat front end surface 220 and is connected to vacuum supply coupling 222 through a passage 224 and a chamber 226 without use of a flap valve to control vacuum conditions as described in U.S. Pat. No. 3,370,877. The arrangement, as hereinafter described in further detail, being such that, as shown in FIG. 8, the bottom end wall portion 17 of a can body member 14 is held against the surface 220 of plate member 214 with abutting substantially sealing engagement established along the annular rim portion 230 of the can body member to provide a vaccuum chamber 234, between surface 220 and the inwardly domed bottom end wall portion 17 connectable to a vacuum source through passage 218.

The passages 218, 224, and chamber 226 are connectable to a conventional vacuum source, such as a vacuum pump and control assembly 236, FIG. 1, at predetermined times during each revolution, through coupling 222, a flexible hose 238, a coupling 240, FIG. 5, a radially extending passage 242 in an annular connecting plate 244 fixed to hub member 89 by suitable fastening members 246 for rotation therewith, an axially extending passage 248, and an arcuate vacuum supply chamber 250 in a non-rotating manifold ring member 252 which is connected to the vacuum source in a manner to be hereinafter described. Pin members 260 are fixedly mounted on an annular ring plate member 262, fixedly non-rotatably mounted on plate member 90 by suitable fastening elements 264, and are loosely received in axially aligned bores 266 in manifold ring member 252 to retain the ring member 252 in non-rotational relationship relative to rotating connecting plate member 244. The bores 266 are larger than the pin members 260 to enable relative axial sliding movement therebetween so that compression spring members 268, mounted circumjacent pin members 260 between axially spaced side surfaces 270, 272, are effective to axially bias the smooth polished side surface 274 of manifold ring member 252 into abutting sealing engagement with the smooth polished side surface 276 of connecting plate member 244.

Referring now to FIGS. 11 and 12, each of the passages 218 of FIG. 4 in each of the support head plates 214 is connectable, at predetermined locations during each revolution, when the associated passage 248 in connecting ring member 244 becomes aligned with the arcuate vacuum chamber 250 which extends arcuately circumferentially approximately 170° in manifold plate member 252 from approximately 6° (at radial line 280) before upper vertical center line 46 to approximately 16° (at radial line 282) before lower vertical center line 45. The vacuum chamber 250 is continuously connected to the vacuum source 236 by a fixedly mounted coupling and a flexible conduit (not shown) extending axially through an axially extending bore in plate member 90 in a manner to be hereinafter described in reference to pressurized air supply means.

The passages 218, 224, 228 are also connectable to a conventional source of pressurized air (not shown) through coupling 222, flexible hose 238, coupling 240, radially extending passage 242, and an axially extending passage 286 which is connectable, at predetermined times during each revolution, to a second axially extending air passage 288 located in non-rotating manifold ring 252 approximately 75° (at radial line 290) below horizontal center line 57. Air passage 288 is controllably connected to a conventional source of pressurized air (not shown) through conventional control valve apparatus (not shown) by a separate coupling member 292, FIG. 5, and flexible conduit 294 extending through a bore 296 in non-rotating plate member 90, the vacuum chamber 250 being connected to the vacuum source by a similar arrangement.

EXTENDABLE AND RETRACTABLE MEANS

Referring now to FIGS. 4 and 5, the extendable and retractable means 52 comprise twelve equally circumferentially spaced axially slidable support shaft members 300 coaxially aligned with the pockets 44 and the sealing means 56, there being one of said shaft members supporting each one of said holding means 54. Each of the shaft members are slidably mounted in a housing member 302 and a bearing sleeve 304 and are slidably non-rotatably held on the outer periphery of hub member 89 for rotation therewith by key members 306.

As shown in FIG. 5, each of the support shaft members 300 are axially movable between extended and retracted positions by the cam follower means 92 which connect the rear end portions of members 300 through supporting connecting flange members 308 on which are mounted cam follower roller members 310, 312 controllably engaged with opposite radially extending annular cam surfaces 314, 316 on the fixedly mounted cam plate means 90. Cam surfaces 314, 316 are contoured to axially extend and retract the support head means 54 at predetermined times during each revolution so as to engage and disengage the can body members relative to the sealing head means 56 as hereinafter described in further detail.

SEALING MEANS

Referring now to FIGS. 8 and 9, sealing means 56 comprises twelve circumferentially spaced units mounted on rotatable plate member 86 in coaxial alignment with the pocket means 44 and the holding means 54. As shown in FIG. 9, each sealing head means 56 comprises can body member flange sealing means in the form of an annular mounting ring member 320 suitably fixedly connected to the rotatable plate 86 within an annular counter bore 322 by suitable fastening elements 324 and within an annular opening 325 in a ring member 326 mounted on the side surface 327 of member 86 circumjacent mounting ring members 320 by suitable fastening elements 328.

An annular resilient flexible sealing ring member 330 of the general type disclosed in U.S. Pat. No, 3,672,208 is fixedly mounted between surface 332 of ring member 320 and surface 334 of plate member 86. Ring member 320 has a radially inwardly extending flange portion 336 with an inwardly tapered front surface 338. Ring member 330, which is made of suitable resilient molded plastic material, such as Neoprene or Urethane or the like, has a U-shaped cross-sectional configuration including first and second identical radially inwardly extending axially spaced annular flange portions 340, 342 connected by axially extending rim portion 344 so as to be reversible. The rim portion 344 is abuttingly sealingly received on annular surface 345 of member 320. The side surface of the inner flange portion is abuttingly received on surface 334 of member 86. The outer flange portion 342 freely extends generally radially inwardly from the rim portion 344 for resilient flexible displacement relative thereto. Flange portions 340, 342 extend radially inwardly substantially beyond the annular outer edge portion 22 of the can body members supported in pockets 44 and terminate in an annular lip portion 346 having a diameter less than the outside diameter of the can body member rim portion 22. Thus, the outer side surface 348 of the outer flange portion 342 is engageable with the outer edge 22 of the flange portion along a relatively small width annular portion of the outer surface 348 of portion 342, FIG. 13. The arrangement is such as to effect sealing engagement therebetween by substantially line contact when the flange portion of the can body member is in engagement therewith. As shown in FIG. 9, during sealing engagement with the rim portion 22, the flange portion 342 is resiliently flexible outwardly bowed so that the outer side surface 348 has a curvature to further assure the desired sealing engagement by substantially line contact. A pressurization chamber 349 is defined by the flange portions 340, 342 and rim portion 344 whereby pressurized air in chamber 349 may be applied to the inner surface 350 of the outer flange portion 342 to further control and obtain the desired sealing engagement with the can body rim portion 22.

PRESSURIZATION MEANS

In order to supply pressurized air to the inside 18 of the can body member and to the chamber 349 of the sealing ring member 330 as well as permit passage of light to the light detection means 62, counter bores 351, 352 extend through plate member 86 in coaxial alignment with pockets 44 and sealing means 56. An annular plate 353 of transparent material, such as Plexiglas or the like, is fixed in bore 351 against a shoulder 354 and sealably mounted therein by an O-ring peripheral sealing member 355 to define a chamber 358 to receive pressurized air from a radially extending passage 360 and to enable the passage of light therethrough from chamber 358 to bore 352. With a can body member mounted on the releasable holding means 54 and with shaft member 300 extended to engage the rim portion 22 of the can body member with the sealing lip portion 342, a closed pressure chamber means is defined by the transparent annular plate 353, bore portion 351, the sealing ring means 330, and the can body member 14.

In order to pressurize the pressure chamber means at predetermined times, each bore portion 351 is connectable by a radially inwardly extending passage 360 in member 86 to an axially extending passage 362 or 363, FIGS. 3 and 11, in member 86, which open through side surface 364. A manifold arcuate segment member 366, FIG. 3, having two radially offset circumferentially extending arcuate pressure chambers 368, 370, is held in sealing abutting engagement on surface 364 by spring means 372 mounted circumjacent retaining pin members 374 carried by a non-rotatable support plate 376 fixed to another non-rotatable support plate member 378 by suitable fastening elements 380 and spacer elements 382. The arrangement is such that alternate ones of the pressure chamber means 358 are connected to pressure chambers 368, 370 by varying the length of alternate passages 360 and the radial location of alternate passages 362 and 363 as illustrated in FIG. 11. In this manner, a source of air pressure (not shown) at, for example, between 10 psi and 15 psi is connected by suitable passage means (not shown) to manifold chambers 368, 370 and at predetermined times passages 362, 363 are aligned with chambers 368, 370 to deliver air pressure to the pressure chamber means for purposes to be hereinafter described. In addition, at predetermined times the passages 362, 363 are located in circumferentially spaced relationship to the manifold member 366, which is in the form of an arcuate segment, whereat the pressure chamber means is vented to the atmosphere. As shown in FIG. 11, chambers 368, 370 extend circumferentially approximately 55° from a position, represented by radial line 280 prior to the upper vertical center line 46 to a position slightly beyond the test station represented by radial line 383. It is noted that a porton 384 of axial passage 360 is extended radially outwardly beyond chamber 358 for manufacturing purposes and is suitably sealed as by a threaded closure.

LIGHT DETECTOR MEANS

Referring now to FIG. 3, the light detector means 62 comprises a conventional photo-multiplier tube assembly (not shown) suitably connected to the control circuitry of the testing apparatus (not shown) for purposes to be hereinafter described.

A tubular support housing 385 is non-rotatably adjustably mounted in a bore 386 in support plate member 378 in coaxial alignment with sealing means 56 by a mounting plate 387 and suitable fastening elements 388. A central bore 389 is adapted to receive and support the conventional photo-multiplier tube assembly therewithin. An access cover 390 is provided at one end of the housing 385 and an annular attachment flange portion 392 is provided at the other end. An annular mounting plate 394, having an annular bearing ring member 396 suitably fixedly attached thereto, is fixedly mounted on flange portion 392 by suitable fastening elements 398. Connecting coaxial bores 400, 402 provide light passages and the interface of members 392, 394 is sealed against passage of light by a sealing ring member 404. The bearing ring member 396 is made of good bearing polymer plastic material and has a side surface 406 adapted to slidably sealably engage the adjacent side surface 364 of member 86 thereby preventing the passage of light into housing 385 except through transparent window plate 353 from chamber 358 in member 86. The support housing 385, mounting plate 394, and bearing ring member 396 are axially resiliently biased toward surface 364 by compression springs 407 mounted on pin members 408 adjustably supported on plate 387 by suitable fastening elements 409.

LIGHT APPLYING MEANS

Referring now to FIGS. 6 and 14, in the presently preferred embodiment, the light applying means 60, located at the test station, comprise seven elongated florescent lamps 412, 413, 414, 415, 416, 417, 418. A first pair of axially extending lamps 412, 413 and associated reflector device 429 are mounted on the cover member 78 approximately 30° on one side of the test station and a second pair of axially extending lamps 414, 415 and associated reflector device 422 are mounted on cover member 78 on the other side of the test station. A single outer center lamp 416 and associated reflector device 424, extending generally tangentially to the path of movement of the transfer wheel means, are mounted on cover member 78 directly above the test station. A pair of inner center lamps 417, 418 and associated reflector device 426, extending generally tangentially to the path of movement of the transfer wheel means, are mounted on a bracket assembly 428 non-rotatably supported on the end portion 429 of bracket 188 directly below the test station. It has been determined that florescent lamps, such as arranged in FIGS. 6 and 14, provide a substantially uniform illumination intensity pattern about the can body at the test station without requiring the use of reflectorized machine surfaces as disclosed in prior art apparatus. In fact, all surrounding metallic machine surfaces are anodized to provide black non-reflecting coloring which provides more uniform test results. As shown in FIG. 6, each of the axially extending reflector devices 420, 422 are arranged to specifically direct a portion of the light from the associated lamps at the radially innermost half area 429 of the can body member. As shown in FIG. 14, each of the circumferentially tangentially extending reflector devices 424, 426 are arranged to direct a portion of the light from the associated lamps at both the flange end of the can body member in the general annular area 430 and to a lesser extent at the bottom end of the can body member in the area 431, with there being a high concentration of reflected light directed at the specific annular area 432 of engagement of the rim portion 22 with the sealing lip portion 342. Thus, any pinhole or crack type defects in the can body member will transmit light into the inside 18 of the can body member 14 where any such transmitted light will be detected by the photo-multiplier tube through chamber 358 and window 353. In addition, any cracks in the flange portion 20 of the can body member will permit transmission of light into chamber 358 and any substantial dents will permit passage of light between the rim portion 22 and the sealing lip portion 342 into the chamber 358 for detection by the photo-multiplier tube.

DISCHARGE CHUTE MEANS

Referring now to FIGS. 2, 4 and 7, the discharge chute means 66 comprises vertically extending axially spaced side plate members 436, 437, an outer vertically extending end plate member 438, which may be removed or further outwardly spaced if desired, and an inner inclined vertically extending end plate member 439 which define a vertically downwardly extending chute passage 440. Side plate members 436, 437 are axially spaced apart a distance slightly larger than the axial length of the can body members, as illustrated in FIG. 4, and are located axially outwardly of the rotating transparent plate members 82, 84 in substantial vertical alignment with the inner side surfaces 441, 442, respectively, of ring member 326 and plate member 94. As shown in FIG. 7, the uppermost portion 443 of side plate member 436 terminates about 7° below horizontal center line 57 with an inner portion 444 located radially inwardly of the pockets 44 and an outer portion 445 spaced radially outwardly of the transparent plate members a distance sufficient to enable passage of the can body members thereby. A curved upper surface 446 of side plate 436 extends circumferentially downwardly in radially inwardly spaced and tangential relationship to pocket surfaces 106. The uppermost surface 447, FIG. 2, of side plate member 437 is downwardly curved and extends substantially tangentially to the peripheral surface of guide plate member 94. The upper portion 488, FIG. 2, of inner end plate member 439 terminates radially outwardly of the transparent plate members 82, 84 below the upper end of the unloading chute means 68. Thus, a circumferentially extending defective can body member inlet opening is defined at the upper end of the discharge chute means between fixed side plate 436 and rotating plate 94. An outlet opening 449, FIG. 4, at the bottom of the passage 440 is connected to an enlarged chute passage 450 defined in part by an outwardly curved discharge chute portion 451 in the lower housing portion 34 and having a terminal portion 452, FIG. 2, extending beyond the housing portion for placement of defective can body members in a collection bin (not shown).

UNLOADING CHUTE MEANS

Referring now to FIGS. 4, 7 and 12, the unloading chute means 68 comprises a generally horizontally extending downwardly inclined (e.g., approximately 15°) elongated rectangular chute passage 454 extending from an inlet opening 455 adjacent plate members 436, 437, 439 of chute means 66 to an outlet opening 456. The lower end of the chute passage 454 is constructed similarly to the upper end of the infeed chute means 48 of FIG. 10 and comprises: an attachment bracket 457 for connection to gravity type conveyor means (not shown) for removal of can body members; a pair of spaced elongated adjustable guide plate members 458, 459; a first pair of lower round spaced elongated guide rail members, one of which is shown at 460, FIG. 7; a pair of upper round elongated guide rail members, 461, 462, FIG. 4; and a support bracket 463 which are mounted on a bracket 464 fixed to the housing means 32. The first pair of lower guide rail members 460 terminate at 466 and the upper guide rail members 461, 462 terminate at 468.

A second pair of lower round spaced elongated guide rail members 470, 471, are coaxially aligned with and form an extension of guide rail members 460. Guide rail members 470, 471 extend between and are fixedly mounted at one end on a transversely downwardly extending plate member 472, which extends therebetween, and at the other end on a pivotally movable hinged cross plate 473 pivotally connected at 474 to a fixed hinge cross plate 475 fixedly mounted across rail members 460 on bracket 464 to provide hinge means for enabling pivotal movement of guide rail members 470, 471 and end plate 472, as indicated by arrow 476 between a normal upper transfer position (shown in FIG. 7) forming an extension of rail members 460 and a downwardly displaced position (not shown). A tension spring means 478, connected at one end to a shaft member 479 fixed to and extending across rail members 470, 471 and at the other end to adjustment bolt member 480 attached to bracket 463, resiliently biases the rail members 470, 471 and end plate 472 toward the upper transfer position while permitting pivotal downward movement by downwardly directed forces as may be encountered in the event of a malfunction (e.g., jamming) during the unloading of can body members. The first and second pairs of axially spaced lower guide rail members 460, 470, 471 rollably slidably guideably engage the outer peripheral surfaces of the side wall portions 16 of and support can body members as illustrated at 482. The side plate member 458 and rail members 470, 471 extend upwardly beyond lower vertical center line 45 approximately 16° to radial line 290, FIG. 12. The upper portions 484 of rail members 470, 471 are located radially outwardly slightly beyond the outer peripheral surfaces of the can body members carried in the pockets 44 while extending substantially tangentially relative thereto. An upper plate member 486 having a lower guide surface 488 aligned with the lower surfaces of upper rail members 461, 462 is fixedly attached to bracket 463 and extends upwardly beyond lower vertical center line 45 approximately 8° with the upper portion 490 thereof located radially inwardly slightly beyond the surfaces 106 of the pockets 44 while extending substantially tangentially to the circular path of movement of the radially innermost portion of surface 106. The upper terminal portion of the plate member 486 may be curved to provide guide ramp means 492 for facilitating movement of the can body members thereon from the transfer wheel means. Side guide plate member 458 is substantially vertically aligned with side plate 436 of chute means 66 in axially outwardly spaced relationship to the adjacent rotating transfer wheel member 82. The upper terminal portion 494 of member 458 extends radially inwardly beyond and in substantial overlapping relationship with the pockets 44 to form a continuation of surface 446 of side plate member 436 for confining axial outward movement of the flange portion 20 of the can body members. Side guide plate member 459 is substantially vertically aligned with rotating plate member 94 and has an inclined upper terminal end portion 496 located radially adjacent and extending generally tangentially relative to the outer peripheral surface of plate member 94 so that the bottom rim portions 230 of the can body members are axially outwardly confined between the chute passage inlet opening 455 and the side plate 459 by plate member 94.

OPERATION

In the presently preferred embodiment of the aforedescribed apparatus, the infeed chute means 48 is connected to a continuous supply of drawn and ironed aluminum can body members 14 which have a formed flange 20 and which are supposed to have a printed ink label on the exterior peripheral surface of the side wall portion. In normal continuous operation, the solenoid operated pins 176 associated with the infeed chute 48 are withdrawn so that such can body members 14 are stacked in the chute for continuous gravity feed movement therethrough. In the event that it is desired to interrupt the continuous gravity feed of the can body members, the solenoid means 174, 175 may be actuated to extend pins 176 into engagement with the can body member, one pin entering the opening 19 and extending into the interior of an axially aligned can body member in chute passage 130, the pins 176 being located on the chute in a position to be axially aligned with one of the can body members therein.

In continuous operation of the apparatus, the drive shaft means 36 is continuously rotated in the direction of the arrows and causes continuous rotation of the transfer wheel means 42. All loading, testing, and unloading functions are performed during one revolution of the transfer wheel means.

During each revolution, empty pockets 44 are rotated past the infeed means 48 whereat one can body member is gravity loaded into each pair of axially aligned pockets 44 on the transparent plate member 82, 84. As indicated in FIG. 11, the initial loading occurs along radial line 169 at approximately 50° before upper vertical center line 46. As the can body member is carried further upwardly from the infeed means, the seating means 51 is effective to fully seat and maintain the can body member on arcuate segment surfaces 106 of the pockets. The seating means brushes 200, 201 are initially effective at a first rotational position 502 located at about 45° before upper vertical center line 46 and substantially fully seat the can body member in the next 5° of generally upward rotation while being continuously effective for about 38° of rotation.

The unprinted can body member detector means 64 is located at a second rotational position 504 at about 30° beyond the first position. The detector means is a self contained conventional retroreflective photo detector unit having a light source for applying light to the outer peripheral surface of the side wall portion 16 of the can body member and having a light detection means for generating a defective can body member control signal upon reflection of a predetermined level of light from the outer peripheral can body member surface indicative of the absence of a printed ink label thereon. The defective can body member control signal is utilized to subsequently cause discharge of the unprinted can body member into discharge chute means 66 as hereinafter described.

The extendable and retractable means 52, associated with each of the aligned pairs of pockets 44, are initially actuated at a third rotational position 506 about 40° before the upper vertical center line 46 and are gradually axially, slidably displaced, during approximately the next 40° of generally upward rotation, from the fully retracted position to the fully extended position at about the time of reaching the upper vertical center line 46. As the means 52 are extended, abutment surface 220 on releasable holding means 54 abuttingly engages the can body member bottom wall portion 17 and axially displaces the can body member relative to the arcuate surface segments 106 of the aligned pockets 44 and relative to the seating means 51 which maintains the can body member on and in slidable engagement with the arcuate segment surfaces 106. The axial movement of the means 52 continues until the flange portion 20 is located in abutting engagement with the flexible sealing lip portion 342 of sealing means 56 as shown in FIG. 9, at approximately the upper vertical center line rotational portion 508.

When, or preferably slightly before, the can body member has been axially shifted to locate the flange portion 20 in engagement with the flexible sealing lip portion 342, vacuum is applied to the releasable holding means 54 by alignment of the vacuum passage 248 in connecting plate 244 with the arcuate vacuum chamber 250 in manifold member 252. As shown in FIG. 11, the vacuum passage 248 becomes aligned with vacuum chamber 250 at rotational position 510 along radial line 280 about 6° before the vertical center line 46 so that vacuum holding of the can body member is effected before beginning the generally downward rotation after center line 46. The vacuum chamber 250 extends circumferentially about 170° and terminates at radial line 282 about 16° before the lower vertical center line 45 so that the vacuum is continuously applied to the releasable holding means for about 170° of rotation to effect vacuum holding of the can body members on the releasable holding means unless sooner terminated as hereinafter described.

In addition, when, or preferably slightly before, the can body member has been axially shifted to locate flange portion 20 in engagement with the flexible sealing lip portion 342, pressurized air is applied to chamber 358 and the interior of the can body member by alignment of the associated one of the air passages 362, 363 in member 86 with the associated one of the arcuate air chambers 368, 370 in manifold member 366. As shown in FIG. 11, the associated air passages and air chambers become aligned along radial line 280 about 6° before vertical center line 46 so that pressurization of the sealing lip portion 342 and the interior of the can body member is initiated before beginning the generally downward rotational movement beyond center line 46. As shown in FIG. 11, the associated air passages and air chambers remain aligned until reaching radial line 512 after about 50° of rotation beyond center line 46. By the time the can body member reaches the test position 514 along radial line 383, a pressurization of between 7 to 14 psi has been effected, the amount of pressurization being variably controllable so that varying test effectiveness may be obtained with higher pressurization resulting in a lower standard of acceptability and lower pressurization resulting in a higher standard of acceptability of can body members.

As shown in FIG. 13, in a maximum defect detection, minimum pressure condition, the radial flange portion 342 has a convexly outward curvature such that the curved outer surface 348 thereof engages substantially only the inner annular edge 516 of the rim portion 22 of the can body member 14. Thus, substantially the entire exterior surface area of the flange portion 20 is exposed to light and all of the interior surface area remains uncovered to enable passage of light through any openings or cracks in the flange portion into chamber 358 and through transparent plate 353 to the light detection means 62. The curvature of flange portion 342 and the amount of area of engagement between exterior surface 348 and flange portion 20 can be varied by varying the air pressure in chamber 349 resulting in variations in the amount of force applied on the interior surface 350 in the general direction of the arrow 518. In a minimum defect, maximum pressure condition, the area of engagement between exterior surface 348 and flange portion 20 is increased so that minor defects in the rim portion 22 are not detected.

Thus, as the pressurized can body member is carried into alignment with the light testing means 62, any light passing from outside the can body member through any pin holes in the wall portions or through cracks in the flange portion 20 or between the sealing lip portion 342 and the rim portion 22 will be sensed by the photomultiplier tube and a defective can body member signal will be generated for purposes to be hereinafter described.

As soon as the test has been completed, the application of pressurized air to chamber 358 is terminated at rotational position 520 along radial line 512, FIG. 11. Then the extendable and retractable means 52 begin axial movement from the extended position to the retracted position and the axial movement is completed during about the next 40° of rotation so as to be located in the fully retracted position by the time the can body member reaches rotational position 522 along horizontal center line 57. During the axial movement from the extended position to the retracted position, the can body member is held on the releasable holding means 54 by vacuum application through passage 218 and chamber 234 against the can body member bottom wall portion 17. Thus, the tested can body member is carried axially and slidably axially displaced relative to the aligned pockets 44 so as to be located in the retracted position illustrated in FIG. 8. In the retracted position, the flange portion 20 is axially spaced a substantial distance from the sealing means 56 and plate member 86 and the bottom wall portion 17 is located relatively closely axially adjacent the side surface 442 of guide plate 94.

Shortly after the can body member is carried generally downwardly, beyond the horizontal center line 57, at rotational position 524 along radial line 290 10° below center line 57, the air passage 286 in member 244 is rotated into alignment with air passage 288 in manifold member 252. The flow of pressurized air in passage 288 is controlled by conventional valve means (not shown) actuable in response to a defective can body member control signal from the non-printed ink label detector means or from the light transfer means 62 to permit flow of pressurized air therethrough. Thus, as air passage 286 begins to become aligned with air passage 288 at rotational position 528 along radial line 529 at about 7° below horizontal center line 57 and when fully aligned at rotational position 524 about 10° below center line 57, pressurized air is delivered to passage 218 in the releasable holding means 54 to dissipate the vacuum and blow-off a defective can body member.

When a defective can body member is released from the releasable holding means 54 at about rotational position 530, the inertial force on the can body member being carried by the rotating plate members 82, 84 causes the can body member to be separated from the pockets 44 and removed from the transfer wheel means in a generally vertical downward direction along a path of downward movement generally tangential to the circular path of movement of the pockets as indicated by arrow 532. The side surface 442 of guide plate member 94 is effective to axially confine the downward movement of the defective can body member after release from the releasable holding means. In addition, the side wall 436 of the discharge chute means 66 axially opposite guide plate member 94 extends upwardly and terminates at 443 above the radial line 529, whereat application of pressurized air begins, so as to also axially confine the defective can body member during downward movement in chute passage 440.

In no defective can body member signal has been generated, the vacuum is continuously applied to the releasable holding means 54 until the can body member reaches the unloading chute means 68. As shown in FIG. 12, the upper inlet end of the unloading chute means extends beyond the lower vertical center line 45 about 16° so as to be substantially coterminus with vacuum chamber 250 along radial line 290. After vacuum passage 248 has been disconnected from vacuum chamber 250, air passage 286 is rotated into alignment with an air passage 534 at rotational position 536 along radial line 538. The passage 534 is continuously connected to a source of pressurized air (not shown) by suitable coupling and conduit means (not shown) similar to the means 292, 294, 296 of FIG. 5. As shown in FIG. 12, air passage 534 is located about 10° before lower vertical center line 45. The upper surfaces 540 of the unloading chute rail members 470 extend generally tangentially relative to the circular path of movement of the pockets 44 at the radial line 538 so that as the can body members are released from the releasable holding means 54, the inertial force of the can body members is directed substantially parallel to the upper surfaces of the unloading chute means 68, as indicated by arrow 542, to enable removal of the can body members from the pockets of the transfer wheel means by inertial force and the effect of gravity. As the released can body member is moved further toward the vertical center line 45, the upper guide plate 486 is effective to disassociate the can body member from the pockets 44 by relative movement between the can body member and surfaces 108, 114 of the plate members 82, 84. The can body members are rapidly discharged into chute passage 454 and rapidly move through the chute passage to outlet opening 456 which may be connected to a gravity type chute conveyor system (not shown). If a malfunction, such as jamming of can body members, occurs in the unloading operation, creating a high force condition, the rail members 470 will be downwardly pivoted against the bias of spring 478 to enable removal and discharge of can body members toward the discharge passage 440 and actuate a limit switch (not shown) to terminate operation of the apparatus.

Thus, methods and apparatus have been provided for very rapid and very effective testing of can body members during one revolution of the transfer wheel means. Some of the inventive concepts, such as the pressurization of the can body member and the flange portion 342 of the sealing means 56 during testing, may be adaptable for use in testing methods involving apparatus other than disclosed hereinbefore. In addition, the methods and apparatus of the presently preferred embodiment of the inventive concepts hereinbefore disclosed may be utilized in whole or in part for testing other types of container members including body members of three piece can type containers and end closure members for either two piece or three piece can type containers. Furthermore, the inventive concepts may be variously otherwise modified and adapted for use in alternative embodiments thereof and for use with other types of articles. Consequently, it is intended that the following claims be construed to include such alternative embodiments except insofar as limited by the prior art.

We claim:

1. A machine for continuous testing of one piece can body members having a sidewall portion, and a bottom wall portion at one end defining a container cavity, and an opening at the other end, and a formed flange portion at the other end surrounding the opening for subsequent association with a can closure member; the machine being adapted for testing the can body member for defects including pin holes in the sidewall portion and the bottom wall portion, and unwanted deformation and cracks in the flange portion, and comprising:

frame and housing means for supporting and housing the machine components;

horizontally extending rotatable shaft means rotatably supported by said frame and housing means and providing a central axis of rotation;

motor means for causing continuous rotation of said rotatable shaft means;

can body member transfer wheel means mounted on said shaft means for rotation therewith and for carrying can body members in a circular path thereabout;

a plurality of pocket means circumferentially spaced about the outer periphery of said transfer wheel means for receiving a can body member in each pocket means and for transferring each can body member along said circular path during a portion of each revolution of said transfer wheel means, each of said pocket means being carried generally upwardly during 180° and generally downwardly 180° during each revolution of said transfer wheel means;

in-feed means mounted on said frame and housing means for loading one can body member in each of said pocket means during the last 90° of the generally upward movement of said pocket means during each revolution of said transfer wheel means;

light applying means for applying light to the exterior surfaces of each can body member in each of said pocket means, the light applying means being non-rotatably mounted relative to said transfer wheel means and located to provide a continuous light zone during the first 90° of the generally downward movement of said pocket means during each revolution of said transfer wheel means;

discharge chute means for receiving defective can body members from said transfer wheel means during the last 90° of the generally downward movement of said pocket means during each revolution of said transfer wheel means;

unloading chute means located generally beneath said transfer wheel means for receiving non-defective can body members from said transfer wheel means during the last part of the last 90° of the generally downward movement and/or the first part of the first 90° of the generally upward movement of said pocket means during each revolution of said transfer wheel means;

extendable and retractable means mounted on said shaft means for rotation therewith and being associated with each of said pocket means for axially moving a can body member in each of said pocket means between a first retracted position and a second extended position during a portion of each revolution of said transfer wheel means;

releasable holding means associated with each of said extendable and retractable means for abutting and releasable holding engagement with the bottom wall portion of a can body member in each of said pocket means during a portion of each revolution of said transfer wheel means;

sealing means mounted on said shaft means for rotation therewith and being associated with each of said pocket means and each of said extendable and retractable means for sealable engagement with the flange portion of non-defective can body members carried in each of said pocket means and releasably held by said holding means, the holding means being operative to effect holding engagement with the bottom wall of said can body member and the extendable and retractable means being operative from the first retracted position to the second extended position to effect sealable engagement of the flange portion of each can body member with the associated sealing means prior to movement of each can body member to said light zone;

light detection means non-rotatably mounted relative to said transfer wheel means and being located for successive axial alignment with each of said pocket means and the opening in the can body member carried thereby opposite said sealing means in the light zone for receiving light only from said light applying means through the can body member and between the flange portion and the sealing means and for generating a control signal upon receipt of light therefrom;

said extendable and retractable means being operative from the second extended position to the first retracted position to retract each can body member from sealable association with said sealing means after downward movement beyond said light detection means prior to reaching said discharge chute means during each revolution of said transfer wheel means;

defective can body member release control means effective in response to said control signal from said light detection means for releasing each defective can body member after beginning the first part of the last 90° of the generally downward movement of said transfer wheel means and before reaching said discharge chute means during each revolution of said transfer wheel means and for enabling downward discharge of defective can body members into said discharge chute means by centrifugal force of said transfer wheel and force of gravity; and non-defective can member release control means effective as each non-defective can body member approaches said unloading chute means for releasing each non-defective can body member and for enabling discharge of non-defective can body members into said unloading chute means by centrifugal force and force of gravity during each revolution of said transfer wheel means.

2. The invention as defined in claim 1 and further comprising:

pressurization means associated with each of said sealing means for applying pressurized air to said sealing means for obtaining minimal sealing area engagement between said sealing means and the flange portion of said can body members and for applying pressurized air through the opening to the interior of said can body member to outwardly flex the side wall portion and the bottom wall portion to enhance the passage of light through openings therein.

3. The invention as defined in claim 2 and wherein said pressurization means comprising:

first passage means connected to a source of pressurized air for supplying pressurized air; and second passage means connected to each of said sealing means and connectable to said first passage means when each associated sealing means and pocket means are located in said light zone for pressurizing said sealing means and a can body member associated therewith in the light zone and prior to movement into axial alignment with said light detection means.

4. The invention as defined in claim 1 and wherein said defective can body release control means comprising:

first pressurized air passage means connectable to a source of pressurized air for supplying pressurized air in response to a defective can body member control signal generated by said light detection means when and while the defective can body member causing generation of the signal is located at said discharge chute means;

a second pressurized air passage operably connected to said releasable holding means and being connectable to said first pressurized air passage means when and while the defective can body member causing generation of the signal is located at said discharge chute means for releasable actuation of said releasable holding means for releasing the defective can body member by application of pressurized air to said releasable holding means.

5. The invention as defined in claim 1 and wherein said non-defective can body member release control means comprising:

first pressurized air passage means connected to a source of pressurized air;

a second pressurized air passage means operably connected to said releasable holding means and being connectable to said first pressurized air passage means when and while a non-defective can body member is located at said unloading chute means for releasable actuation of said releasable holding means for releasing the non-defective can body member by application of pressurized air to said releasable holding means.

6. The invention as defined in claim 1 further adapted for testing of one piece can body members for printed material normally provided on the outer peripheral side wall surface of the can body member, and further comprising:

non-printed can body member detection means non-rotatably mounted relative to said transfer wheel means and being located adjacent the side wall portion of said can body members while being carried by said pocket means for providing a control signal in response to light reflected from the outer peripheral surface of non-printed can body members and for actuating said first control means to discharge non-printed can body members into said discharge chute means during each revolution of said transfer wheel means.

7. The invention as defined in claim 6 and wherein said non-printed can body detection means comprising:

a light sensor means non-rotatably mounted between said transparent plate members and located radially inwardly of said pocket means for applying light to and for receiving light from the outer peripheral surface of a can body member and for generating a defective can body member control signal only in response to light reflected from an unprinted can body member.

8. The invention as defined in claim 1 and wherein said can body transfer wheel means comprising:

a pair of axially spaced radially extending transparent plate members, and said pocket means being located on the periphery of said plate members.

9. The invention as defined in claim 8 and wherein the other outer surfaces of said can body transfer wheel means which are exposed to light in said light zone being of non-reflective material.

10. The invention as defined in claim 8 and wherein each of said pocket means comprising:

an arcuate surface segment having a center on a radial line extending from said central axis of rotation and having a radius of curvature approximately equal to or slightly larger than one-half the outside diameter of the side wall portion of the can body members, a larger portion of said arcuate surface segment being located on the trailing side of said radial line and extending from said radial line generally opposite the direction of movement of said transfer wheel means at least 90° to provide a surface portion extending substantially transversely to the circular path of movement of can body members in said pocket means from said radial line in the general direction of movement of said transfer wheel means, a smaller portion of said arcuate surface segment being located on the leading side of said radial line and extending substantially less than 90° to enable discharge of can body members from said transfer wheel means at said discharge means and at said unloading means.

11. The invention as defined in claim 10 and wherein each of said pocket means further comprises:
an elongated curved ramp surface intersecting said smaller portion of said arcuate surface and extending circumferentially and radially outwardly therefrom in the direction of movement of said transfer wheel means to guide can body members from said in-feed chute means to said arcuate surface segment; and
a short length arcuate surface defining the radially outermost portion of said transfer wheel means and connecting the elongated curved ramp surface of each pocket means to the arcuate surface segment of the next adjacent pocket means.

12. The invention as defined in claim 8 and wherein said infeed chute means comprising:
a four sided guide chute passage defined by spaced parallel upper and lower guide rail means and spaced parallel guide plate means and having a rectangular cross-sectional configuration corresponding to the peripheral configuraton of said can body members;
the upper surfaces of said lower guide rail means of said guide chute being outwardly and upwardly curved relative to said transfer wheel means; and
a can body member inlet opening at the upper end of said guide chute and a can body member outlet opening at the bottom end of said guide chute.

13. The invention as defined in claim 12 and further comprising:
first lower guide rail means for rollably guideably supporting can body members for gravity feed movement from said inlet opening toward said outlet opening; and
second lower guide rail means extending from said outlet opening between said parallel spaced transparent plate members and being upwardly curved toward said arcuate segment surfaces of said pocket means for guiding a can body member into each of said pocket means.

14. The invention as defined in claim 13 and further comprising:
upper support surface means on said second lower guide rail means being upwardly curved and extending generally tangentially toward said arcuate segment surfaces of said pocket means for engaging the outer peripheral surface of said side wall portion of said can body member and guiding said can body member into said pocket means and onto said arcuate segment surfaces thereof.

15. The invention as defined in claim 14 and further comprising:
guide surface means on each of said guide plate means of said guide chute extending from said outlet opening toward said transfer wheel means for guiding a can body member into each of said pocket means; and
an upper guide plate means having lower guide surface means being upwardly curved and extending generally tangentially to the circular path of movement of said pocket means for enabling said can body members to be transferred from said outlet opening to said pocket means and carried along the circular path of movement by said pocket means.

16. The invention as defined in claim 12 and further comprising:
can body member releasable holding means mounted on said guide chute for selectively engaging a can body member therewithin to prevent downward movement of can body members therethrough.

17. The invention as defined in claim 1 and comprising:
a non-rotatable empty pocket sensing means mounted between said transparent plate means in juxtaposition to said infeed means with a sensor mounting member located closely adjacent and spaced slightly radially inwardly of an arcuate plane including the radially innermost portions of said arcuate segment surfaces of said pocket means for sensing the outer peripheral surface of the side wall portion of said can body members on the radially innermost portions of said arcuate segment surfaces of said pocket means.

18. The invention as defined in claim 10 and further comprising:
seating means non-rotatably mounted relative to said transfer wheel means and located in juxtaposition to said infeed means for seating each can body member on the surfaces of said pocket means during the last 90° of the generally upward movement of said transfer wheel means.

19. The invention as defined in claim 18 and wherein said seating means comprising:
resilient flexible guide means non-rotatably mounted in radially outwardly spaced relationship to said pocket means between said transparent plate means in juxtaposition to said infeed means and extending circumferentially from said infeed means in the direction of movement of said pocket means for engaging the outer periphery of the sidewall portion of can body members being carried from said infeed means by said pocket means and for resiliently radially inwardly biasing said can body members toward said arcuate segment surfaces of said pocket means to effect engagement between said arcuate segment surfaces and the outer periphery of the side wall portion of the can body members.

20. The invention as defined in claim 19 and wherein said resilient flexible guide means comprising:
at least one brush member having a multitude of generally radially inwardly extending bristles defining a curved inner surface with a first end portion next adjacent said infeed means and a second end portion circumferentially upwardly spaced from said inlet feed means, the curved inner surface of said bristles being in constant resilient biasing engagement with the outer periphery of said side wall portions of said can body members carried past said brush means by said pocket means.

21. The invention as defined in claim 19 and wherein:
said flexible guide means being in constant resilient biasing engagement with the outer peripheral surface of the side wall portion of said can body members throughout the length of said flexible guide means.

22. The invention as defined in claim 1 and wherein said releasable can body member holding means comprising:

a transparent support member associated with each of said pocket means and being mounted in coaxially alignment with said pocket means and being continuously rotatable therewith in coaxial alignment therewith during continuous rotation of said transfer wheel means;

flat radially extending outer abutment surface means on each transparent support member next adjacent said pocket means for abutting sealable engagement with the bottom wall portion of non-defective can body members and for defining a vacuum chamber between said transparent support member and the bottom wall portion of non-defective can body members;

a connecting passage in said transparent support member connected to said vacuum chamber; and pressurized air and vacuum supply and control means connectable to each connecting passage for alternately creating a vacuum in said vacuum chamber and supplying pressurized air to said vacuum chamber at predetermined times during each revolution of said transfer wheel means to hold non-defective can body members on said transparent support member by vacuum during a portion of each revolution, and to release non-defective can body members from said transparent support member by application of pressurized air at a predetermined position during each revolution, and to release defective can body members from said transparent support member by application of pressurized air at another predetermined position during each revolution.

23. The invention as defined in claim 22 and wherein said pressurized air and vacuum supply and control means comprising:

a non-rotatable support plate member mounted on said frame and housing means in axially spaced relationship to said transfer wheel means;

a non-rotatable manifold member mounted next adjacent said non-rotatable support plate member;

an arcuate segment vacuum supply chamber means in said second non-rotatable manifold member for supplying vacuum to hold can body members on said transparent support plate means;

a source of vacuum connected to said vacuum supply chamber means for maintaining a vacuum therein;

a rotatable flow control plate member mounted next adjacent said non-rotatable manifold member and being connected to said shaft means for continuous rotation therewith relative to said non-rotatable manifold member;

a first radially extending side surface on said non-rotatable manifold member and a second radially extending side surface on said rotatable flow control plate member, the first and second side surfaces being parallel and located in abutting slidable chamber sealing engagement during continuous rotation of said flow control plate member relative to said non-rotatable manifold member;

separate vacuum flow passage means in said rotatable flow control plate for connecting each vacuum chamber to said arcuate segment vacuum supply chamber during movement of said transparent support plate member in the light zone and from the light zone to the non-defective can body member unloading chute means and for supplying vacuum for holding non-defective can body members on said releasable holding means until reaching said non-defective can body member unloading chute means;

a first pressurized air passage in said non-rotatable manifold member and connected to a continuous supply of pressurized air;

separate pressurized air flow passage means in said rotatable flow control plate member for connecting each vacuum chamber to said first pressurized air passage when said releasable holding means reaches said non-defective can body unloading chute means to effect positive release of non-defective can body members at said non-defective can body member unloading chute means;

a second pressurized air passage in said non-rotatable manifold member and being connectable to a continuous supply of pressurized air;

a flow control means associated with said second pressurized air passage for connecting said second pressurized air passage to a continuous supply of pressurized air for a predetermined period of time upon receipt of a control signal from said light detection means indicative of a defective can body member and for otherwise preventing flow of pressurized air therethrough;

said second pressurized air passage being connectable to said separate pressurized air flow passage prior to being connectable to said first pressurized air passage when said releasable holding means reaches said defective can body member discharge means to effect positive release of defective can body members at said defective can body member discharge means;

mounting means for mounting said non-rotatable manifold member for axial movement; and spring means for biasing said non-rotatable manifold member into continuous sealing engagement with said rotatable flow control plate member.

24. The invention as defined in claim 1 and wherein said extendable and retractable means comprising:

a hub member fixedly mounted on said shaft means for continuous rotation therewith;

slide housing apparatus mounted in circumferentially spaced relationship on said hub member for rotation therewith, there being one slide housing for each of said pocket means located in general axial alignment therewith;

a shaft member mounted in each slide housing for axial sliding movement therewithin between an extending position and a retracted position relative to said pocket means;

one of said releasable holding means being mounted on one end of each shaft member for releasably holding a can body member and axially moving a can body member relative to said pocket means toward and away from said sealing means; and cam means operatively associated with each shaft member for extending said shaft member and axially moving said holding means and a can body member held thereon toward said sealing means to effect sealing engagement between the flange portion of the can body member and the sealing means during movement through said light zone and prior to alignment with said light detection means, and for retracting said shaft member and axially moving said holding means and the can body member held thereon away from said sealing means to enable removal of the can body member from said pocket means at aid discharge chute means or at said unloading chute means.

25. The invention as defined in claim 24 and wherein said cam means comprising:
a cam plate member non-rotatably mounted next adjacent the other end of said shaft members; and
roller cam apparatus mounted on the other end of each of said shaft members in operable engagement with said cam plate member.

26. The invention as defined in claim 1 and wherein said sealing means comprising:
an annular rotatable support plate member mounted on said shaft means for continuous rotation therewith in fixed relationship to said transfer wheel means and having a radially outwardly extending inner side surface next adjacent said transfer wheel means and a radially outwardly extending outer side surface next adjacent said light detection means;
a multiplicity of equally circumferentially spaced transverse passages extending through said annular support plate member between the side surfaces thereof and being equally radially outwardly spaced from said central axis of rotation;
said transverse passages being equal in number to the number of said pocket means and being coaxially aligned therewith;
a flexible sealing member mounted on the inner side surface of said annular support plate member in circumjacent relationship to each of said transverse passages; and
a flexible resilient sealing lip portion on each sealing member defining an annular opening and having an annular outer side surface next adjacent said transfer wheel means for abutting sealable engagement with the flange portion of a can body member,and having an inner side surface for application of axially outwardly directed sealing force.

27. The invention as defined in claim 26 and further comprising:
a transparent window member sealably fixably mounted in each of said transverse passages next adjacent said outer side surface of said annular support plate member and being axially spaced from said flexible sealing member to define a presurized air and light transmission chamber therebetween; and
pressurized air supply and control means connectable to each pressurized air and light transmission chamber for supplying pressurized air to said chamber during sealable association of said lip portion with the flange portion of said can body member in said light zone and for applying axially outwardly directed force on said inner side surface of said lip portion to effect a minimum area of sealing engagement between said annular outer side surface of said lip portion and the flange portion of non-defective can body members, and for pressurization of the interior of can body members in sealed association with said lip portion to outwardly flex the side wall portion thereof to enhance the detection of pin holes therein.

28. The invention as defined in claim 27 and wherein said pressurized air supply and control means comprising:
a non-rotatable manifold member non-rotatably mounted next adjacent said outer side surface of said annular support plate member;
arcuate segment supply chamber means in said manifold member for supplying pressurized air;
a source of pressurized air connected to said arcuate segment supply chamber means and maintaining pressurized air therein; and
a supply passage in said annular support plate member for and connected at one end to each pressurized air and light transmission chamber and connectable at the other end to said arcuate segment supply chamber means to supply pressurized air to said pressurized air and light transmission chamber for effecting a minimal area of sealable association of said lip portion with the flange portion of said can body member in said light zone.

29. The invention as defined in claim 28 and wherein said arucate segment supply chamber means comprising:
two radially spaced arcuate segment supply chambers;
each supply passage an axially extending passage portion extending transversely through the outer side surface of said annular support plate member and connectable to one of said supply chambers; and
alternate ones of said air pressurization and light transmission chambers being connectable to the same one of said supply chambers through alternate ones of the supply passages.

30. The invention as defined in claim 1 and wherein said light applying means comprising:
a plurality of outer lamp members mounted in radially outwardly spaced relationship to said transfer wheel means and said sealing means above and on opposite sides of said light zone detection means; and
at least one inner lamp member mounted below said light zone in radially inwardly spaced relationship to said pocket means in generally radial alignment with said light detection means.

31. The invention as defined in claim 30 and wherein:
there being at least one radially aligned outer lamp member mounted in generally radial alignment with said inner lamp member and said light detection means; and
there being at least one outer circumferentially spaced lamp member mounted in circumferentially spaced relationship to and on one side of said radially aligned outer lamp member and at least one other circumferentially spaced outer lamp member mounted in equal circumferentially spaced relationship to and on the other side of said radially aligned outer lamp member.

32. The invention as defined in claim 31 and wherein said lamp members being elongated fluorescent tubes.

33. The invention as defined in claim 32 and wherein at least some of said tubes extending generally tangentially and the other of said tubes extending generally transversely to said circular path of movement of said pocket means.

34. The invention as defined in claim 33 and wherein the longitudinal axis of said inner lamp member and the longitudinal axis of said radially aligned outer lamp member being parallel and extending generally tangentially to the circular path of movement of said pocket means; and
the longitudinal axes of the circumferentially spaced outer lamp members being parallel and extending generally transversely to the circular path of movement of said pocket means.

35. The invention as defined in claim 34 and wherein there being two of said radially aligned outer lamp members, and two circumferentially spaced outer lamp members on one side of and two circumferentially spaced outer lamp members on the other side of said radially aligned outer lamp members.

36. The invention as defined in claim 30 and further comprising:
an access opening in said upper portion of said frame and housing means;
said access opening extending in generally circumferential radially outwardly spaced relationship to said transfer wheel means and said sealing means above said light zone;
a movable cover means mounted on said frame and housing means for movement between a closed position and an open position relative to said access opening and for supporting said outer lamp members in proper relationship to said light zone in the closed position and for substantially sealing said access opening to entry of outside light into the light zone in the closed position; and
non-rotatable bracket means mounted on the upper portion of said frame and housing means and extending generally radially inwardly beneath said pocket means and having a lamp support portion located beneath said pocket means for supporting said inner lamp member.

37. The invention as defined in claim 27 and wherein said light detection means comprising:
a first non-rotatable support plate member mounted on said frame and housing means in axially spaced relationship to said annular support plate member for said flange sealing means;
a mounting passage in said support plate member extending transversely therethrough and being coaxially alignable with said flange sealing means and said pocket means during continuous rotation thereof;
a light detector housing axially slidably adjustably mounted in said mounting passage and having a light receiving opening in one end thereof next adjacent said flange sealing means;
a bearing plate member mounted circumjacent said light receiving opening;
radially extending bearing surface on said bearing plate member in slidable light sealing bearing engagement with said outer side surface of said annular rotatable support plate member for said flange sealing means;
a light transmission passage in said bearing plate member coaxially aligned with said light receiving opening in said light detector housing and coaxially alignable with each light transmission window in each of said transverse passages in said annular rotatable support plate member for said flange sealing means;
axially movable mounting means for mounting said light detector housing and said bearing plate member in said mounting passage; and
spring means for axially biasing said light detector housing and said bearing plate member toward said annular rotatable support plate member for said flange sealing means to maintain said radially extending bearing surface on said bearing plate member in sealable abutting relatively slidable association with the outer side surface of said annular rotatable support plate member.

38. The invention as defined in claim 8 and wherein said discharge chute means comprising:
a vertically extending first discharge passage means providing a discharge passage located beneath a horizontal plane including said central axis of rotation for receiving defective can body members and defining a downwardly extending free fall path for defective can body members therewithin.

39. The invention as defined in claim 38 and further comprising:
an inlet opening at the upper end of said discharge passage means extending circumferentially parallel to said transfer wheel means and an outlet opening at the lower end of said discharge passage;
said discharge passage and said inlet opening being defined by vertically extending plate members including a pair of axially spaced side plate members extending parallel to said transparent plate members of said transfer wheel means;
an outer end plate member connecting said side plate members and extending generally vertically transversely to said transparent plate members of said transfer wheel means and being located radially outwardly of said transfer wheel means a distance sufficient to enable passage of can body members thereby, and an inner plate member connecting said side plate members and being inclined relative to said outer end plate member and extending generally transversely to said circular path of movement of said pocket means, one of said side plate members opposite said holding means upwardly terminating radially inwardly of the outer periphery of said transparent plate members and extending radially inwardly beyond said pocket means to limit axial movement of defective can body members away from said holding means upon release from said holding means, the other of said side plate members adjacent said holding means terminating radially outwardly of said holding means and said pocket means to enable rotation of said holding means with a non-defective can body member; and
said inner end plate member terminating radially outwardly of said transfer wheel means a distance sufficient to enable passage of a non-defective can body member thereby.

40. The invention as defined in claim 39 and further comprising:
a vertically extending second discharge passage located beneath said outlet opening of said first discharge passage;
an inlet opening in said second discharge passage connected to said outlet opening in said first discharge passage;
an outlet opening in said second discharge passage spaced downwardly and outwardly of said inlet opening; and
curved guide means extending between said inlet opening and said outlet opening in said second discharge passage for receiving defective can body members discharged from said first discharge passage means by free fall and guidably downwardly and outwardly carrying said defective can body members by gravity force.

41. The invention as defined in claim 10 and wherein said unloading chute means comprising:

discharge passage means providing a discharge passage extending generally tangentially to the circular path of movement of said pocket means and downwardly and outwardly relative thereto in the direction of the circular movement thereof for guidably rotatably slidably carrying non-defective can body members away from said transfer wheel means.

42. The invention as defined in claim 41 and further comprising:
an inlet opening at the upper end of said discharge passage means extending generally transversely to the circular path of movement of said pocket means and an outlet opening at the lower end of said discharge passage means;
said discharge passage and said inlet opening being defined by axially spaced vertically extending side plate members and vertically spaced upper and lower guide rail members;
said side plate members being axially spaced a distance to movably receive and confine the can body members therebetween; and
the upper terminal portions of one of said side plate members next adjacent the bottom wall portion of the can body members extending upwardly beyond the central axes of said pocket means and being located in general radial alignment with said pocket means and can body members carried thereon to axially movably confine the can body members therebetween.

43. The invention as defined in claim 42 and further comprising:
an upper guide plate member associated with said upper guide rail members and having a terminal portion extending upwardly beyond said arcuate segment surfaces between and in axially inwardly spaced relationship to said transparent plate members to remove can body members from said pocket means during continuous rotation of said transfer wheel means.

44. The invention as defined in claim 43 and further comprising:
a downwardly inclined bottom surface on the upper terminal portion of said upper plate member providing upper guide ramp means for changing the circular direction of movement of said can body members and for guiding said can body members into said discharge passage means.

45. The invention as defined in claim 44 and further comprising:
the upper terminal portion of said lower guide rail members extending upwardly to a point of general tangential coincidence with the lowermost outer peripheral surface portion of the side wall portion of said can body members carried in said pockets on said holding means in said circular path of movement to supportably rollably guidably carry can body members from said pocket means upon release from said holding means.

46. The invention as defined in claim 45 and further comprising:
said lower guide rail members having movable upper portions and fixed lower portions;
pivotally mounting means supporting said upper portions for pivotal movement between a first upper position in alignment with said lower portions and a second downwardly displaced position extending generally transversely to said lower portions and providing a connecting passage to said defective can body discharge means; and
spring means associated with said upper portions to bias said upper portions to the first position while enabling movement to the second position upon application of excessive force caused by jamming of can body members in said discharge passage means.

47. The invention as defined in claim 45 and further comprising:
the upper terminal portion of said upper plate member being circumferentially spaced beyond the upper terminal portion of said lower guide rail members in the direction of movement of said transfer wheel means.

48. The invention as defined in claim 35 and further comprising:
light reflector means associated with each of said lamp members for establishing a predetermined light pattern at the annular area of engagement between the flange portion of a can body member and said sealing means and for providing sufficient light all along the annular area to detect all defects in the flange portion.

49. The invention as defined in claim 48 and wherein said light reflector means further providing for establishing a predetermined light pattern at the bottom wall portion of a can body member to provide sufficient light along the bottom wall portion to detect all defects therein.

50. Apparatus for testing wall portions of a container member, or the like, having an annular flange portion for defects and comprising:
sealing means of resiliently flexible material for engaging the annular flange portion of the container member;
light applying means for applying light to the wall portions and annular flange portion of the container member to be tested;
light detection means for receiving light passing through the wall portions of the container member to be tested and through the open end portion of the container member, and between the sealing means and the annular flange portion of the container member; and
pressurization means for applying pressurized air against said sealing means to establish a predetermined amount of area engagement between said sealing means and the flange portion of the container member.

51. The invention as defined in claim 50 and wherein:
said sealing means having a sealing surface engageable with said flange portion of the container member; and
said pressurization means being effective to cause said sealing means to have a convex configuration and said sealing surface to have a convex curvature for establishing a minimum area of sealing engagement between a limited portion of said sealing surface and said flange portion of the container member.

52. The invention as defined in claim 51 and wherein:
the convex configuration of said sealing means and the convex curvature of said sealing surface being variable in accordance with the pressure of the pressurized air.

53. A method of testing wall portions of container members or the like, having a flange portion, for defects, and comprising the steps of:

sealing the flange portion of the container member by engagement with a resilient flexible sealing means;

pressurization of an interior surface of the container member and also the flexible sealing means by pressurized air;

applying light to an exterior surface of the container member; and detecting light passing through the wall portions of the container member from the exterior surfaces.

54. The method as defined in claim 53 and further comprising:

varying the pressure of the pressurized air to vary the area of engagement between the resilient flexible sealing means and the flange portion of the container.

55. The method of continuous testing of can body members, having a side wall portion and a bottom wall portion and an opening at one end and a formed flange portion surrounding the opening for association with a can closure end member, for defects, including pin holes in the sidewall portions and unwanted deformation and cracks in the flange portion, comprising the steps of:

continuously loading can body members to be tested on continuously rotating transfer wheel apparatus at a location where the transfer wheel apparatus is moving in an upward direction;

effecting sealable engagement between the flange portion of the can body members and flexible sealing apparatus rotatable with the rotating transfer wheel apparatus, holding the can body member by application of vacuum to the exterior surface of the bottom wall portion of the can body member during continuous rotation of the transfer wheel apparatus while the flange portion is in sealable engagement with the flexible sealing apparatus during continuous rotation of the transfer wheel apparatus.

locating light detector apparatus in axial alignment with the can body member adjacent the opening therein during continuous rotation of the transfer wheel apparatus;

uniformly applying light to all exterior surfaces of the can body member and the area of sealable engagement between the flange portions and the flexible sealing apparatus when the light detector apparatus is in axial alignment with the can body member during continuous rotation of the transfer wheel apparatus;

generating a control signal by the light detector apparatus whenever light passes through a pin hole in the side walls or between the flange portion and the flexible sealing apparatus and the light is received by the light detection apparatus during continuous rotation of the transfer wheel means;

disengaging the flange portion of the can body member from sealable engagement with the flexible sealing apparatus after location of the light detector apparatus in axial alignment with the can body member during continuous rotation of the transfer wheel apparatus while the can body member is being moved in a downward direction thereby;

terminating the application of vacuum to the exterior surface of the bottom wall portion of defective can body members at a discharge position, after disengaging the flange portion of the can body member from sealable engagement with the flexible sealing apparatus, in response to a control signal from the light detector apparatus indicating a defect, while the can body member is being moved in a downward direction during continuous rotation of the transfer wheel apparatus;

removing the defective can body member from the transfer wheel apparatus, after terminating the application of vacuum to the exterior surface of the bottom wall portion, by downwardly directed movement as the can body member is being moved in a downward direction during continuous rotation of the transfer wheel apparatus;

maintaining the application of vacuum to the exterior surface of the bottom wall portion of non-defective can body members beyond the discharge position during continuous rotation of the transfer wheel apparatus;

terminating the application of vacuum to the exterior surface of the bottom wall portion of non-defective can body members at an unloading position, located beyond the discharge position, during continuous rotation of the transfer wheel apparatus; and removing the non-defective can body members from the transfer wheel apparatus, after termination of the application of vacuum to the exterior surface of the bottom wall portion, by association with generally radially outwardly extending guide chute apparatus located at least in part below the continuously rotating transfer wheel apparatus.

56. The invention as defined in claim 55 and further comprising:

effecting pressurization of the flexible sealing apparatus when light detector apparatus is in axial alignment with the can body member during continuous rotation of the transfer wheel apparatus to flex the sealing apparatus and establish a predetermined minimum area of sealing engagement between the sealing apparatus and the flange portion.

57. The invention as defined in claim 55 and further comprising:

effecting pressurization of the interior of the can body member when the light detector apparatus is in axial alignment with the can body member during continuous rotation of the transfer wheel apparatus to flex the side wall portion to enhance the detection of pin holes therein.

* * * * *